US011267876B2

(12) United States Patent
Kagey et al.

(10) Patent No.: US 11,267,876 B2
(45) Date of Patent: Mar. 8, 2022

(54) USE OF BETA-CATENIN AS A BIOMARKER FOR TREATING CANCERS USING ANTI-DKK-1 ANTIBODY

(71) Applicant: Leap Therapeutics, Inc., Cambridge, MA (US)

(72) Inventors: Michael H. Kagey, Arlington, MA (US); Cynthia A. Sirard, Cambridge, MA (US)

(73) Assignee: Leap Therapeutics, Inc., Cambridge, MA (US)

( * ) Notice: Subject to any disclaimer, the term of this patent is extended or adjusted under 35 U.S.C. 154(b) by 130 days.

(21) Appl. No.: 16/345,191

(22) PCT Filed: Oct. 26, 2017

(86) PCT No.: PCT/US2017/058555
§ 371 (c)(1),
(2) Date: Apr. 25, 2019

(87) PCT Pub. No.: WO2018/081437
PCT Pub. Date: May 3, 2018

(65) Prior Publication Data

US 2019/0284264 A1 Sep. 19, 2019

Related U.S. Application Data

(60) Provisional application No. 62/413,198, filed on Oct. 26, 2016.

(51) Int. Cl.

| | |
|---|---|
| ***A61K 39/395*** | (2006.01) |
| ***C07K 16/18*** | (2006.01) |
| ***A61P 35/00*** | (2006.01) |
| ***A61K 31/337*** | (2006.01) |
| ***A61K 45/06*** | (2006.01) |
| ***C12Q 1/6886*** | (2018.01) |
| *A61K 39/00* | (2006.01) |

(52) U.S. Cl.
CPC ............ *C07K 16/18* (2013.01); *A61K 31/337* (2013.01); *A61K 39/3955* (2013.01); *A61K 45/06* (2013.01); *A61P 35/00* (2018.01); *C12Q 1/6886* (2013.01); *A61K 2039/505* (2013.01); *A61K 2039/55* (2013.01); *C07K 2317/21* (2013.01); *C07K 2317/565* (2013.01); *C07K 2317/76* (2013.01); *C12Q 2600/106* (2013.01); *C12Q 2600/156* (2013.01)

(58) Field of Classification Search
CPC combination set(s) only.
See application file for complete search history.

(56) References Cited

U.S. PATENT DOCUMENTS 7,446,181 B2 * 11/2008 McCarthy .............. C07K 14/47 530/388.23
8,148,498 B2 * 4/2012 Chedid .................. A61P 19/08 530/387.3
2012/0201810 A1 * 8/2012 Ng Liu .................. C07K 16/18 424/133.1
2019/0284264 A1 9/2019 Kagey et al.

FOREIGN PATENT DOCUMENTS

| | | | |
|---|---|---|---|
| EP | 2963114 | A1 | 1/2016 |
| WO | WO-2007/084344 | A2 | 7/2007 |
| WO | WO-2008/097510 | A1 | 8/2008 |
| WO | WO-2010/117980 | A1 | 10/2010 |
| WO | WO-2018/081437 | A1 | 5/2018 |

OTHER PUBLICATIONS

Yu et al (J of Hepatology, 2009, 50:948-957).*
Chen et al (Molecular Cancer, 2013, 12:157, internet pp. 1-14).*
Chamorro et al (The EMBO Journal, 2005, 24:73-84).*
Ding et al (PLoS ONE, May 2014, 9:e95307, internet pp. 1-9).*
ClinicalTrial.gov Trial NCT02013154 initial Dec. 2013 posting (5 pages).*
ClinicalTrial.gov Trial NCT01457417 first posted 2011 and last updated Sep. 2016 (15 pages).*
Sato et al (Cancer Research, 2010, 70:5326-5336).*
Clements et al (Cancer research, 2002, 62:3503-3506).*
Bendell et al., "Phase I study of DKN-01, an anti-DKK1 antibody, in combination with paclitaxel (pac) in patients (pts) with DKK1+ relapsed or refractory esophageal cancer (EC) or gastro-esophageal junction tumors (GEJ).", J Clin Oncol, 34(Suppl.4):111 (2016).
Cho et al., "Dickkopf-1 inhibits thyroid cancer cell survival and migration through regulation of beta-catenin/E-cadherin signaling", Mol Cell Endocrinol, 366(1):90-98 (2013).
Fillmore et al., "Nmi (N-Myc interactor) inhibits Wnt/beta-catenin signaling and retards tumor growth.", Int J Cancer, 125(3):556-564 (2009).
Ilson et al., "Paclitaxel given by a weekly 1-h infusion in advanced esophageal cancer", Annals of Oncology, 18(5):898-902 (2007).
International Search Report and Written Opinion for International Application No. PCT/US2017/058555 dated Feb. 7, 2018.
Katoh et al., "Molecular genetics and targeted therapy of WNT-related human diseases", Int J Mol Med, 40(3):587-606 (2017).
Strickler et al.: "Biomarker studies in a phase I trial of DKN-01 in advanced esophageal cancer", J Clin Oncol, 35 (Suppl.5): 161 (2016).
Tai et al: "Targeting the WNT Signaling Pathway in Cancer Therapeutics", Oncologist, 20(10):1189-1198 (2015).

(Continued)

*Primary Examiner* — Laura B Goddard
(74) *Attorney, Agent, or Firm* — Foley Hoag LLP

(57) ABSTRACT

A method of treating a cancer in a subject in need thereof is disclosed. The cancer can be an esophageal cancer, a uterine cancer, a liver cancer, or a cholangiocarcinoma. The method comprises administering to the subject an effective amount of an anti-Dkk-1 antibody or antigen binding-fragment thereof, wherein the subject is determined to have a constitutively activating mutation of the beta-catenin protein.

13 Claims, 12 Drawing Sheets

Specification includes a Sequence Listing.

(56) References Cited

OTHER PUBLICATIONS

Veeramachaneni et al., "Down-regulation of beta catenin inhibits the growth of esophageal carcinoma cells.", J Thorac Cardiov Sur, 127(1):92-98 (2004).
Wang et al., "FRAT1 overexpression leads to aberrant activation of beta-catenin/TCF pathway in esophageal squamous cell carcinoma," Int J Cancer, 123(3):561-568 (2008).
Anonymous, "DKK1 ", Wikipedia, Jun. 5, 2020, XP55723680, Retrieved from the Internet: URL:https://en.wikipedia.org/wiki/DKK1 retrieved on Aug. 19, 2020].
Anonymous, "Wnt signaling pathway", Wikipedia, Jun. 19, 2020, XP55723679, Retrieved from the Internet: URL:https://en.wikipedia.org/wiki/Wnt_signaling_pathway [retrieved on Aug. 19, 2020].
Biau et al., "Statistics in Brief: The Importance of Sample Size in the Planning and Interpretation of Medical Research," Clinical Orthopaedics and Related Research, 466(9):2282-2288 (2008).
Chamorro et al., "FGF-20 and DKK1 are transcriptional targets of β-catenin and FGF-20 is implicated in cancer and development," The EMBO Journal, 24(1): 73-84 (2005).
Colquhoun, "An investigation of the false discovery rate and the misinterpretation of p-values," Royal Society Open Science, 1(3):140216 (2014).
CTNB1_HUMAN (P35222) // https://www.uniprot.org/uniprot/P35222#sequences // Integrated into UniProtKB/Swiss-Prot: Feb. 1, 1994.
D'Amico et al., "Dickkopf-related protein 1 (Dkk1) regulates the accumulation and function of myeloid derived suppressor cells in cancer," Journal of Experimental Medicine, 213(5): 827-840 (2016).
Karrison et al., "Design of Phase II Cancer Trials Using a Continuous Endpoint of Change in Tumor Size: Application to a Study of Sorafenib and Erlotinib in Non-Small-Cell Lung Cancer," Journal of the National Cancer Institute, 99(19):1455-1461 (2007).
Kimura et al., "CKAP4 is a Dickkopfl receptor and is involved in tumor progression," The Journal of Clinical Investigation, 126(7): 2689-2705 (2016).
Kimura et al., "CKAP4, a DKK1 Receptor, Is a Biomarker in Exosomes Derived from Pancreatic Cancer and a Molecular Target for Therapy," Clinical Cancer Research, 25(6): 1936-1947 (2019).
Krause et al., "An unexpected role for a Wnt-inhibitor: Dickkopf-1 triggers a novel cancer survival mechanism through modulation of aldehyde-dehydrogenase-1 activity," Cell Death & Disease, 5: e1093 (2014).
Niida et al., "DKK1, a negative regulator of Wnt signaling, is a target of the β-catenin/TCF pathway," Oncogene, 23: 8520-8526 (2004).
Sada et al., "Dynamic palmitoylation controls the microdomain localization of the DKK1 receptors CKAP4 and LRP6," Science Signaling, 12(608): eaat9519 (2019).
Sancho et al., "The Wnt antagonist DICKKOPF-1 gene is a downstream target of β-catenin/TCF and is downregulated in human colon cancer," Oncogene, 24:1098-1103 (2005).
Shang et al., "The regulation of ?-catenin activity and function in cancer: therapeutic opportunities," Oncotarget, 8(20):33972-33989 (2017).
Shinno et al., "Activation of the Dickkopfl-CKAP4 pathway is associated with poor prognosis of esophageal cancer and anti-CKAP4 antibody may be a new therapeutic drug," Oncogene, 37: 3471-3484 (2018).
Tao et al., "Dickkopf-1 (DKK1) promotes invasion and metastasis of hepatocellular carcinoma," Digestive and Liver Disease, 45(3): 251-257 (2013).
Thudi et al., "Dickkopf-1 (DKK-1) stimulated prostate cancer growth and metastasis and inhibited bone formation in osteoblastic bone metastases," Prostate, 71(6): 615-625 (2011).
Wang et al., "Dickkopf-1 is frequently overexpressed in ovarian serous carcinoma and involved in tumor invasion," Clinical & Experimental Metastasis, 28: 581-591 (2011).
Hirotsu et al., "Targeted and exome sequencing identified somaticmutations in hepatocellular carcinoma," Hepatology Research, 46: 1145-1151 (2016).
Junzo et al., "β-Catenin Intracellular Localization and Search of Gene Aberrance in Wnt Signal Transduction System Constituting Factor in Esophageal Cancers," Nihongekagakkai Zasshi (Journal of Japan Surgical Society), 2002, 103 Extra-Special Edition, p. 350 (PP0172) with English Translation.
Ninomiya et al., "Expression of β-Catenin, β-Catenin and APC Gene Mutations, and Hypermetylation of Promoter Region in Esophageal Cancers," Nihonshokakibyougakkai Zasshi (Journal of The Japanese Society of Gastroentrology), 2001, 98 Extra-Special Edition Meeting, p. A456 (Sho(Digestive) p. 34) with English Translation.

* cited by examiner

| Patient ID | Response[1] | Cycles on Treatment[1] | CTNNB1 Mutation | Predicted Effect | Allelic Frequency | Gene Panel |
|---|---|---|---|---|---|---|
| 105-023 | PR (-73%) | 16+ cycles (on going) | Exon 2-4 deletion | Stabilizing | Unknown | Foundation One |
| 104-004 | PR (-67%) | 13+ cycles (on going) | Not detected | NA | NA | Archer VariantPlex Solid Tumor |
| 108-003 | PR (-40%) | 10 cycles (off treatment) | C-term truncation: Q27Ter | Unknown | 6% | Archer VariantPlex Solid Tumor |
| 109-008 | PR (-35%) | 3+ cycles (on going) | S45F | Stabilizing | 2% | Archer VariantPlex Solid Tumor |
| 109-003 | SD (-7%) | 9+ cycles (on going) | I35N<br>T41I | Most likely stabilizing<br>Stabilizing | 3%<br>4% | Archer VariantPlex Solid Tumor |
| 104-014 | SD (-6%) | 4+ cycles (on going) | Not detected | NA | NA | Solid Tumor Hotspot NGS |
| 109-001 | SD (-2%) | 3 cycles (off treatment) | Not detected | NA | NA | Archer VariantPlex Solid Tumor |
| 104-016 | PD (13%) | 2 cycles (off treatment) | Not detected | NA | NA | Guardant 360 |
| 104-017 | PD (8%) | 2 cycles (off treatment) | Not detected | NA | NA | Foundation One |
| 104-020 | PD (69%) | 2 cycles (off treatment) | Not detected | NA | NA | Archer VariantPlex Solid Tumor |
| 104-018 | PD (90%) | 2 cycles (off treatment) | D6N | Most likely no effect | 11% | Archer VariantPlex Solid Tumor |
| 104-023 | PD (260%) | 2 cycles (off treatment) | Not detected | NA | NA | Archer VariantPlex Solid Tumor |

[1] Response as of 8/3/16, best response. Cycles are 28 day periods -- treatment delays may prolong or adjust these durations.
Legend: Partial response (PR). Stable disease (SD). Progressive disease (PD).
[2] For the Archer VariantPlex Solid Tumor Gene Panel, the Archer Analysis (version 4.1.0.5) default parameters were used to identify CTNNB1 mutations

FIG. 1

CTNNB1 genomic DNA sequence (includes introns)
(SEQ ID NO: 1)

```
Exon 2
ATGGCTACTCAAGgtttgtgtcattaaatctttagttactgaattggggc 50
tctgcttcgttgccattaagccagtctggctgagatccccctgctttcct
ctctccctgcttacttgtcaggctaccttttgctccatttttctgctcact
cctcctaatggcttggtgaaatagcaaacaagccaccagcaggaatctag
tctggatgactgcttctggagcctggatgcagtaccattcttccactgat
tcagtgagtaactgttaggtggttccctaagggattaggtatttcatcac
tgagctaaccctggctatcattctgcttttcttggctgtctttcagattt
gactttatttctaaaaatatttcaatgggtcatatcacagattcttttttt
tttaaattaaagtaacatttccaatctactaatgctaatactgtttcgta 400
         Exon 3
tttatagCTGATTTGATGGAGTTGGACATGGCCATGGAACCAGACAGAAA
AGCGGCTGTTAGTCACTGGCAGCAACAGTCTTACCTGGACTCTGGAATCC 500
ATTCTGGTGCCACTACCACAGCTCCTTCTCTGAGTGGTAAAGGCAATCCT
GAGGAAGAGGATGTGGATACCTCCCAAGTCCTGTATGAGTGGGAACAGGG
ATTTTCTCAGTCCTTCACTCAAGAACAAGTAGCTGgtaagagtattattt
ttcattgccttactgaaagtcagaatgcagttttgagaactaaaaagtta
gtgtataatagtttaaataaaatgttgtggtgaagaaaagagagtaatag
caatgtcacttttaccatttaggatagcaaatacttaggtaaatgctgaa
                                           Exon 4
ctgtggatagtgagtgttgaattaacctttccagATATTGATGGACAGT 850
ATGCAATGACTCGAGCTCAGAGGGTACGAGCTGCTATGTTCCCTGAGACA
TTAGATGAGGGCATGCAGATCCCATCTACACAGTTTGATGCTGCTCATCC
CACTAATGTCCAGCGTTTGGCTGAACCATCACAGATGCTGAAACATGCAG 1000
TTGTAAACTTGATTAACTATCAAGATGATGCAGAACTTGCCACACGTGCA
ATCCCTGAACTGACAAAACTGCTAAATGACGAGGACCAGgtaagcaatga
catagctagctttttagtctgctttgaagtaaatgctcaaggggagtagt
ttcagaatgtctacccaataccagtacttgaaaactaacgatgtttctga
attcctgtattacagGTGGTGGTTAATAAGGCTGCAGTTATGGTCCATCA
GCTTTCTAAAAAGGAAGCTTCCAGACACGCTATCATGCGTTCTCCTCAGA
TGGTGTCTGCTATTGTACGTACCATGCAGAATACAAATGATGTAGAAACA
GCTCGTTGTACCGCTGGGACCTTGCATAACCTTTCCCATCATCGTGAGGG
CTTACTGGCCATCTTTAAGTCTGGAGGCATTCCTGCCCTGGTGAAAATGC
TTGGgtaagaaaacatgtcagaatgcttgaagctaaaaagtagaagagta 1500
tactcacaatatttctgatgaggctttttcttcttcccagTTCACCAGT
GGATTCTGTGTTGTTTTATGCCATTACAACTCTCCACAACCTTTTATTAC
ATCAAGAAGGAGCTAAAATGGCAGTGCGTTTAGCTGGTGGGCTGCAGAAA
ATGGTTGCCTTGCTCAACAAAACAAATGTTAAATTCTTGGCTATTACGAC
AGACTGCCTTCAAATTTTAGCTTATGGCAACCAAGAAAGCAAGgtaagag
aattattctttatgtggttttcatggagcattggacacctccagtgtcat
gtcattccatgcagtgttcctaacctttttggcaccagggaccagtttcg
tggaaaacagtttttccatgaatgggttgtgggaatggtttctggatgac
accattccacctcagataatcaggcattagattctcatagggagcgtgca
gcctagatccctcgcatgtgcagtccacactagggtttctactcctatga 2000
gactctcatggtgcagttgatctgacaggaggtagagctcaagccaggta
atgctcgctcacctgccacttacctcctgctgtgcagcccagttcatttc
tgttcttttaaatttttgagtttccatatgtaaagcactatgcgaagtag
tagggatatggtaggcaagcttctcttcacacttttgttcttaggtggga
tgtagatgttgggaataataacctaatatttaatttgtgtagtgggaaga 2250
```

FIG. 3A

```
agtggggctatgagggcacataacacaagttgaaactgactctttttgag 2300
ggttcaaggagacctcttggaggaagtgatagttgagttcagtgttcaag
gatgagaagggattcactaggtgaaggttaggtgagaaaacaacatcttt
gaaacgaaggaaggagatggaaagttttgggaatttaagaaatactaata
gtaaggaggaagaaaggtttgaggtgaggctattgagatagacttagcag 2500
atctcatagggctttgtagagcatgtttaaaagcacaatgggaaatttca
gcagaagcctgaaatgatgaaatttgtttttagaaaattggggcagtgtt
gaaagggaagatatacagggaatgaaaggacaagcatgaatgatcatttt
atggtatctgtttttaaggtggatataattaggaaaattaaagggccaaa
tgatgaggagttaagtgccagttctggttcaaattttcagtgaatcagtt
ttgatataactttcatcttagggcattactcttgcctaccaacatagttt
ctaaatttttttcttttggtgtgatcactgtgggaagaaggaaattgggc
ccaaactgatacattgtttggaggactgggatgtctgaatttgagtggaa
tgctttaaaaggacaagttggatagggccccagtatgggggtctgagtga
tggggtccaggaatacatttaggtccaatggcaagctggctgaaattctt 3000
gtataataaaataggttggtaatatggctcttctcagacatgtgatcaag
attccttgactaacaagatatatatatatatctttctagCTCATCATACT
GGCTAGTGGTGGACCCCAAGCTTTAGTAAATATAATGAGGACCTATACTT
ACGAAAAACTACTGTGGACCACAAGCAGAGTGCTGAAGGTGCTATCTGTC
TGCTCTAGTAATAAGCCGGCTATTGTAGAAGCTGgtaagtatatgtatct
attctgagtcttgtgtatagcatctgcagttctaattagattacttttct
taggaaaaggtggtagaactttaactactgaaaataaatggtcctattca
gtttgcagccaagatttacattcagagtacctgtcatctggattgtagct
aaatatttaaggctagtttaggtagagttcttattatccatcaaaaatga
tggcatatgttttgcttaataaaatttgtttgtaatttcagttttgagta 3500
aacctaagatttgctaacagagctgtgaatttataggagaaaagacaaat
tctaatatagtacagttttatgtaaagtgattgctttattagtagatgct
catgagcagtttttgttttgttttaacttttaggttccgggtaatgtgca
ggcttgttatataggtaaattgcatgtcacaggggtttcgtgtgcagatt
attttgtcacccaggcagtaagtattgtacccaataggtagtttttcagt
tctttacctcccacccgtaagtaggccccagtgtctgttgttcccttctt
tgtgcccgtgtgtactcagtgtttacctcccacttataagtgagaacatg
tggtatttggtttttctattcctatgttagtttgcttaggataatggcctc
cagctccatccatgttgctgaggaagacatcttggtatttttttatggct
gcttagtattccatagtatatatgtaccacatttttctttatctagtctac 4000
cattgatgggcatttaggttaattccatatctttgctattgtgaataatg
ctgcagtgaacatatgcatgcatgtgtctttatggtaaaaagatttcttt
ttctttgggcatatacctaataataggattgctggattgaatggtaattc
tgtcaggtttttttgagaaatcaccaaattgctttccacaatggctgaact
aatttactttcccaccagcagtgtataagcattctcttttctcagcaacc
tcaccagcatctgtcatttttttgactttttattagtagccattctaactg
gtgtgagacggtatctcattgtggtttttgatttgcatttctctaatgatc
agtgatgtcgagcttttcttcatatgtttcttggccacttgtatgtcttc
ttttgaaaagtgtctgttcatgtcctttgcccactttttaatggggttgt
tctttttttgcttgttaatttaagtttattgtaaactctggatattagacc 4500
tttgtcagatgcatagtttgccagtactttctcccatgccagtactttct
cccattctgtaggttgtctgtttactctgttgatttcttttgctgcgcag
aagctctttatactgtcccatttgtcagtttttgtttttgttgcaacttc
tcttggcatcttcgtcatgaaatctttgccaggtcttatgtccagaatgg
tatttcctaggttatcttgcagagtttttacagttttaagttttatattt
aagtctttaatccattctgagttgatttttgtacatcatgtaaggatggg
gtgcagtttcaatcttggatgtggctagccagttatcccagcaccattta 4750
```

FIG. 3B

```
ttgaatagggagtcctttccccattgcttgtttttgtttacttgttaggt 4800
gtgcggcctaacttctgggctttcttttctgttccattggtctctgtgtc
tgtttgtataccagtaccatgctgtgattgtaaccttgtattaacagtat
agcttgaagttgggtaaagtgattcctccagttttgttctttttgcttag
gattgccttggctattcaggctctttttttgggttcatatgaatttttaaa 5000
tagttttttttttaattatgtgaagaatgccattggtagtttggtaggaat
agcattgaatctgtgaattgctttgggctgtatggccattttaacaatat
tgattcttcctgccatgaaatagaatgtttttttcatttgttggtgtcatc
tctgatttctttgagcagtgtttttttgtaattctcattgtagagatcttt
cacctccctggttagttgtattcctaggtattttattctttttgtggctt
tggtaaatgggattgcattcttgatttggcttgcagcttggatgttgttg
gtgtctagaaatgcttctgacttttgtacattgattttatatcctgaaa
ctttgctgaagtttattggatcaaggagcttttgggcagagattatgggg
ttttctaggtatagaatcatattgtttgcaaacagacttcctatttggat
gcatttttctttctcttgcctgattatgagcagtgttttgccctgatattc 5500
tgtattctcagtgaatagatgtcgtctaagtatgagaaacaatttttttc
tattctgagtatttttaagaaggcaacttatatgtggtactttgtatatt
gtgtatgttggcaattggggaaaagaatagatggtttgtactagggcctc
ttgggttctgtgtgtgtgtgtgtgtgtgtgtgtgtgtgtcatgaaaacag
ttacttttttagctaccaagcatttttttctcctttcagtaacccacctaac
aacatttactcagaatttcaaagcaagcttcaaatcagtattgaaagaag
gaaaaatataaaggcatttaatggaagaaaatgttgggaataaagtatag
ggctggcaacacttacttttctcacttattgagagtaattttacttggga
atttatgagagagaaagacattatgattgctccaggtaactactggcaga
ggaaccatagtcttggggatagacaaatgtggctgagttcatatagaatg 6000
aggggatgggatgtaaattctgtcagctgttccagcagtaacctgtaatg
taggctaaaaatacagattttgagatttatttaatcagaatccctggagt
gttaatttttatatcaagatctcatagtgttttatttgaagtgacaggga
ggtctgtagatagctggacatgtatgggactggaagcttaggaatcttta
agttcttccaggttattcttatgttcatttgtttattctgaaaatagcat
ctaatgtattttaagaaatggaataggcacatagtatacattgggtaaca
caacagatagggtccccgtgcttaattcttagtcttgtgaaggtgacaaa
aatacttaaaaatatgtgatcctaaattagaatgagtgttatgggagaaa
tgacagcaaatagtgatgagaattaatggggaggggaattgtctagatga
gagggaaaaggtctccttgaaaaggggatgttaagtgggactgcaggatg 6500
agagggaaccgtctcttgtctatatgagaagtgagggttaaacgttttcc
aggtagagaaaaggaacaccatgtgctatgtcttagaaccagggatatcc
agtcttttggcttccctgggccacattggaagaagaataattgtcttggg
ctacacaccaaatacactaatgatagctgatgagctaaaacaaaaaaaaa
ttgcaaaagaatctcataatgtttaagaaagtttacgaatttgtgttggg
ctacattcagagctgtcctaggccatgtggcccatgggctgcaggttgga
caagcttgccttagaaggaaagagattggtcaggcacggtggctcacgcc
tgtaattccagcactttgggaggctgaggtgggcggatcatgaggtcagg
agatcgagaccagcctggctaacacagtgaaaccccatctctactaaaaa
tacaaaaagttagccgggcgtggtggcaggcgcctgtagtcccagctact 7000
tgggaggctgaggcaggagaatggtgtgaacccgggaggcggagcttgca
gtgagctgagatagcgccactgcacttcagcctgggcgacagagtgagac
tctatctcaaaaaaaaaaaaaaagggaaagagattgtggagatccaggtgc
tgaagagaaggtctgcataaacagaacttagtaatgaggtggatggcctg
gtatgaggttgaggttaggtaagcagagccataacatgcaggactttcta
ggttcctataagatagttactactcatggagtttattcatgctttattcc
agctttggagccatagatacagaatactttggtcagtttggaaggctagg 7350
```

FIG. 3C

```
tgggatccaaattctaaacggttcctcagggttatactaaagtatttcta 7400
ttatcttaaaaggatgctgagacactttcgatggttgtttatcaatagca
aagcatcacagtggtgtgtttaaaatattaataatagcattgtatagatt 7500
aacagtttgaatgaccaaaagctagaagaccagactactgagatgttaca
ggctttaggaatgaaatagtttgcttttagaactcaatagcaaagggca
gatgtctgagatgcctgaaagaatcatagaatgtaataatataggagcta
agggagcaaccaaaaacggtttgtggaggggacaacattggtaccatgaa
gataaatggaaccctcagaaggcatccttaattttgaacataataattt
aagaagctgacttaaagtgacttaaaaggtcagtaggtagctggaaatgt
atgatactagaatgcaagagaggcaggctagagatttggaagtttccctc
ttagtatataggggtaagggcagcagggaaggggaggtagaggtgccaca
gagtcatctgtatgggactttttttttttaccctagaactgctgaatcaga
atgtgtgtgttttaaagtctctgtaggccattctgatggacatctggggt 8000
taaaatccattctcttagagttaatagttatgtaaagggagggaatgaag
tcttaaagaggggaaagaaggtagtcatttcacaaatactgagcatcctg
atcatcagtcttacgcagatcattctattagtagctggagctactatgaa
aaaggaacccaacagaggtgatctttgtcttgtagggaaagtggagtaac
ttacactatgaaggagaagtgcagggtaccataagaattacagcagatag
acctcatctgaggaaataaaacagacccgaaagatgaaggagacaaggaa
aagtatctcttactgcattcagaagtgatttaagttgaagatggatgagc
gaagttaatctactatgtgggcattgggcttccatttatactcctttgcc
agagtaaatgtcccccatttaagggtcctaaaggatggaagattgtaaac
cttggaacacatgttttgtagtcagtgaattgtataaagtccctgacagt 8500
aagtgttttcatgccgtctttctggattgttcttaccccaggaatttacc
tagcttctttaggtctttagtcagatgtcaccttcacagtgaggtgacct
aattatctatttaaaatcgcagcccccactccattatttttctccatagcc
ctttaatatcatctgacatactgtatggtttagtttattgtatattttt
ctgcctcttccaactagatcataaattctgagggtaggaacttctgaata
ttttgttcactggtctatctgcagctcagaacaggacctggtactgaat
aaatattttgaaatgattgaatggatgaaaagaaatgagtaataagaat
attacctaagggggacagtggagataacaaaggctttttcggcttaggaa
aggaacagtagctatttgagagtttgtcactagtgaggtgaactggcaaa
gtgaaggaaactgagcaacattctagaaaatgagaggaaatcaaatactt 9000
aggtgaaaggaagtaaactctggaaatacagaaggacacctcctaaggct
agaacagatatttaggattgataggcacttctagctaatgactagggcct
tatatcctttttaatttctagGTGGAATGCAAGCTTTAGGACTTCACCT
GACAGATCCAAGTCAACGTCTTGTTCAGAACTGTCTTTGGACTCTCAGGA
ATCTTTCAGATGCTGCAACTAAACAGgtaaattctgagtaaactggtgcc
atgggaatagagtcaagatgagtatgtgcttgtactgaccatctgtttt
atctccatagGAAGGGATGGAAGGTCTCCTTGGGACTCTTGTTCAGCTTC
TGGGTTCAGATGATATAAATGTGGTCACCTGTGCAGCTGGAATTCTTTCT
AACCTCACTTGCAATAATTATAAGAACAAGATGATGGTCTGCCAAGTGGG
TGGTATAGAGGCTCTTGTGCGTACTGTCCTTCGGGCTGGTGACAGGGAAG 9500
ACATCACTGAGCCTGCCATCTGTGCTCTTCGTCATCTGACCAGCCGACAC
CAAGAAGCAGAGATGGCCCAGAATGCAGTTCGCCTTCACTATGGACTACC
AGTTGTGGTTAAGCTCTTACACCCACCATCCCACTGGCCTCTGATAAAGg
taaattgtcaaagtagaatttacctttgttgcagaattgaaaatgaagca
tctctagctgttggatggctgtctaagcatagtgatcaataagtaggaat
tgtattccttagtaagtaggaagtatggctgcgataggggtaagattctg
aaatgtttgtgtagtcagaactacttttagttgataccaatagatttagt
gtggtgggaattttagggtaagaaaatgattttgttgagttgtatgccag 9900
```

FIG. 3D

```
ttcttccttctgttttcagGCTACTGTTGGATTGATTCGAAATCTTGCC 9950
CTTTGTCCCGCAAATCATGCACCTTTGCGTGAGCAGGGTGCCATTCCACG 10000
ACTAGTTCAGTTGCTTGTTCGTGCACATCAGGATACCCAGCGCCGTACGT
CCATGGGTGGACACAGCAGCAATTTGTGgtaggtaaattcttacagtga
tacctggctatctaaaaggaatgcataaatccaaaggatcctgaacttct
ttctttggtcattggttccccccatccgtcttcctgaagagctaatgaca
aagtaaataaataaataattacacatttctatggctgcagagaaaataag
gcatagtgtggccccagtgatatttccttggacacgtccttcacatggtc
agtcttacaaaggttgggttaggtgtttcataaagtgttctcatttaatt
tacacaaaggcccacttccttaggaagaggtagagtcataatttgagatc
aaatctgtgtaatttcagagcctcttacccttgcctcatcatgcattttg
actataaatatttagcagtccgttttattatcttttctgtgagttaaact 10500
tttttcatggacctaagaatattcagaaataagtagtagcatttctgtac
tcttaaccacaaaaatctcaacctgaagctttgatacaaagtttgtgtct
taaaagtagcttcattaaaagtatagtctaatgacatttctgatttctca
gactttaagaccttattaggttagtttagaaaacaaagatggagcctacc
agaacagatgttaggaatctcattttgctggttgctttgtgtatgtactc
atattggggctttggctttcttcatttattactgttggtattggcccatc
tccatgaggtgacttaatagaacgttgagggcacctttttatttaaatct
cttttctaggaagaagagagtttttgtgtccttgtaagaatcaagttatt
tataaaagctgctaaatgtagcagaataataacccctttaaaactcaaa
tccagaaacaggagaaacagatggtacttacatattgcaaaagctatctt 11000
ccttctatacatgaggctgtcagctgaatagtcttggaagagtgaggagt
gaatttttctgctggcaactcggttagttttagcagttggtgctaaaact
tggcaaagttttcaccaaatacatggaagatatacaaaaatagagggggc
atgtaaaagaaaaacgttgacatagtctgagcattactttctcatcttct
ctttttatatacctttttacccagaatgattggtgcccttactgtaggaaa
gttgtctttgggattcagcgctgtatggaagctctgttgcactgtgtatg
ggggaggggtgctgctttgaattagtgctgccaggaggcctcttttcagt
gacattcaagttaatggaatccttcttccttcctgaactaattgcaagtt
acggggaacttcgggtatataatgtaaataattacagtctaataattgtt
cctcaaactttacagaggagaatgccctgtttgttaaccatgtttctttt 11500
ggcagGAGGGGGTCCGCATGGAAGAAATAGTTGAAGGTTGTACCGGAGCC
CTTCACATCCTAGCTCGGGATGTTCACAACCGAATTGTTATCAGAGGACT
AAATACCATTCCATTGTTTGTGCAGgtatgttttaagtgaagtgttctag
gttttatgtccataaaatttccagattgtaatgactaataacatttcaga
aaattagggaccataatagggttaccaacatttaattttatgaaaattcc
ctacatttttttggtcagtaagagaaacattgagacttgagaagagggagg
agatttcacatttcacttttatgggtgcctagagggggagagctgacctgg
gctgccagaggcagggcatagacccccaaccaattctgggtttttccaaat
cttagatcagttagagctgcctctgaagaaagggtttatagctaaaaaat
attatggaaatccagtgctccagagcattaaacaccccaagacataaaat 12000
tcagagaatattatttactacagtgtgaatgcctcttgcactctgaattg
ggaatgtttgcaccacagtggggggcttgccatgttttagctttagattt
aattaggttttgtttgtgtttttctccttagCTGCTTTATTCTCCCATTGA
AAACATCCAAAGAGTAGCTGCAGGGGTCCTCTGTGAACTTGCTCAGGACA
AGGAAGCTGCAGAAGCTATTGAAGCTGAGGGAGCCACAGCTCCTCTGACA
GAGTTACTTCACTCTAGGAATGAAGGTGTGGgtaagtaaaaaggaaccaa
agcctttagcagatgtgtacattgaagtctcagtttttcctcaagggcct
tttctccttgtctcttagCGACATATGCAGCTGCTGTTTTGTTCCGAAT
GTCTGAGGACAAGCCACAAGATTACAAGAAACGGCTTTCAGTTGAGCTGA
CCAGCTCTCTCTTCAGAACAGAGCCAATGGCTTGGAATGAGgtagggaaa 12500
```

FIG. 3E

```
tgtgagcagttatttatctggtagtttcctagagcaggtatggcagcttg 12550
ttctttcctctcaaaacacttagtacacattcatttgcattgatgtttcc
ctggcttgagtatttcttctttatgctgtctagcaactgctctgaggaag
aactataatacaagctttaaagagtctgttcagaatcattacaaataagt
tgtgttatttaaaattataattcataagggagaaagatgaaaaatgttac
cagattaaagaagatttttcaaaaggatgtaaggaaagaggcagtgttaa
acactgttaagaggacagtttatcagtatttttactaaactttaataaa
acttttctatttgaatttctgctatgaatttttcttcagcatttgtcctc
agtacaggtggttccttgaaacattgtttctaataaaactagaacatcct
gatattttatccattctatagagatcattgatggtacacagacatacagt 13000
ggattatgtttgttgagtgaatggaaagagagattgttaggtttacaacg
atgcagctcttgagaccggagtttaagatcagcctgggcaacatagtgaa
accccatctttagctgggcatggagatggatgcctatagtcctagctact
ggggagacgggggcaggaggattgcttgaacccaggagttaacagactgc
actcagtgacagagccagactccaacacaaaaaaaaaaaaaaaaaaaag
caaattaccagtgagtagtgtgttacttgggtttttaataggcatcttat
taacatgttccaacttgagcccttaactttctccacctaccccttccac
aaacctgttttcactgtcttctctgtcttagttaatgtcagctttgtctg
tccagctgctcaggctaaaactttctttcatataacacatcctatcagc
agctcctgtttgtgggtaggcatttgccttttttttttttttttttttt 13500
aaactgctatatctctagcatgtagaacagtgcctggcagcacataatag
gtgcttaatataatatttgttgaaagaacaagtcagtgagtattttttaat
gtgaggtgcaaagagaaaaaaaaatgtatctttgaggtgtggagttttga
agaacttccattttctaagcatttgtgtaatgttggagttacttgttcct
tttgtaatctgaaagtatgctttaaaaaaaattagtgtacttttgagaat
tttcattttgctttctattcttcccttgctttgtgcatgtttatctagACT
GCTGATCTTGGACTTGATATTGGTGCCCAGGGAGAACCCCTTGGATATCG
CCAGGATGgtatgtgtctcatatttctcgattaactccagatcaagctaa
agttctaaaacttttatcagaagagccggtttgctcatctgggaaaccag
tgttggcagaaaagtagtggcttcaattaaaagcagttcttaaattccag 14000
tcagcaacagtatctttaatggagcacagggaattcagagccacacaatg
agtagcagtaggattacaccaccaacaaatacatgctactgctaggcctc
tgcagtgcaggatgttacaatttacctggctttttattctctttttggcc
agaggactcataatacctttgtctacaagctacccaaggaagataggaaa
actcctgtttctaggctcagatctcgggtgggtttttacatagttgcatt
atcatcagggttttcttgaaaagctaatttaaatctgggtaatgaacatg
gaggatggcatagaccactaacaattataactgtcttacatttataaccg
catctgcttctacctaattatgaaaccactaaagcgcagattcttactgt
gagaaataacatgtcaaccctaagataaaatatgttgaggtttcatggaa
atagtgcctttccttagtacttttgtgggtgtcacttggcctttttgtca 14500
agatagattacacctgccagacctcattattgtcttaatcctccttccca
tgacttctcactgcctaggtggtcacacagtagattcctgcttcttctcc
tcgggaaccccaagtctcttgacaggggtaaatgcagagtgttcagggtt
agactaatgatgtgactaggccctgctggtgtgcctgtctgatggaaata
gatgttatttgtgtagtctcatgggtggcctggcactgagtaattacttg
gctaaagaaagctggaggttgaagaggctagaaagcgttgttttctgaca
agtttgctgctgaactttggatgccctaacctcagtgttaacgtctatgt
ctgcttctctcctctctctttgccttccttcttgcctatttgttgaca
ccctgactcttctagATCCTAGCTATCGTTCTTTTCACTCTGGTGGATAT
GGCCAGGATGCCTTGGGTATGGACCCCATGATGGAACATGAGATGGGTGG 15000
CCACCACCCTGGTGCTGACTATCCAGTTGATGGGCTGCCAGATCTGGGGC
ATGCCCAGGACCTCATGGATGGGCTGCCTCCAGGTGACAGCAATCAGCTG 15100
GCCTGGTTTGATACTGACCTGTAA                           15124
```

FIG. 3F

| Uterine Tumor ID | CTNNB1 Mutation |
| --- | --- |
| TCGA-AP-A0LV-01 | D32G |
| TCGA-BK-A0CB-01 | D32G |
| TCGA-AX-A05U-01 | D32N |
| TCGA-A5-A0GV-01 | D32N |
| TCGA-BG-A0VX-01 | D32N |
| TCGA-BS-A0T9-01 | D32N |
| TCGA-A5-A0GX-01 | D32Y |
| TCGA-B5-A0K6-01 | D32Y |
| TCGA-BG-A0W2-01 | D32Y |
| TCGA-D1-A17S-01 | D32Y |
| TCGA-AX-A05W-01 | G34E |
| TCGA-A5-A0VQ-01 | G34E |
| TCGA-A5-A0GN-01 | G34R |
| TCGA-AP-A0LL-01 | G34R |
| TCGA-BG-A0MU-01 | G34R |
| TCGA-B5-A11F-01 | G34R |
| TCGA-D1-A102-01 | G34R |
| TCGA-D1-A17N-01 | G34R |
| TCGA-BS-A0WQ-01 | G34V |
| TCGA-D1-A17M-01 | G34V,D32N |
| TCGA-AX-A0J0-01 | M553V,S37F |
| TCGA-D1-A16R-01 | Q623E,I35S |
| TCGA-B5-A0JY-01 | R453Q,D32N |
| TCGA-AX-A062-01 | S33C |
| TCGA-BG-A0MO-01 | S33C |
| TCGA-A5-A0R9-01 | S33C |
| TCGA-BS-A0UT-01 | S33C |
| TCGA-D1-A0ZN-01 | S33C |
| TCGA-AP-A05N-01 | S33F |
| TCGA-AX-A05T-01 | S33F |
| TCGA-A5-A0GU-01 | S33F |

| Esophageal Tumor ID | CTNNB1 Mutation |
| --- | --- |
| TCGA-R6-A6XQ-01 | S33A |
| TCGA-R6-A8WG-01 | S37F |
| TCGA-LN-A7HX-01 | R90L |
| TCGA-L5-A4OJ-01 | V136A |
| TCGA-L5-A8NM-01 | X561_splice |
| TCGA-L5-A8NR-01 | Q68* (nonsense/truncating) |
| TCGA-R6-A8W5-01 | E571* (nonsense/truncating) |
| TCGA-VR-AA4G-01 | S681F |
| TCGA-V5-A7RB-01 | K335T |

| Liver Tumor ID | CTNNB1 Mutation |
| --- | --- |
| TCGA-DD-AACP-01 | D32A,S33Y |
| TCGA-EP-A2KC-01 | D32G |
| TCGA-G3-A5SL-01 | D32G |
| TCGA-DD-A73D-01 | D32G |
| TCGA-ED-A7PZ-01 | D32G |
| TCGA-G3-AAV1-01 | D32G |
| TCGA-DD-AACB-01 | D32G |
| TCGA-DD-AAW1-01 | D32G |
| TCGA-UB-A7MD-01 | D32N |
| TCGA-G3-AAV5-01 | D32N |
| TCGA-DD-AAVY-01 | D32N |
| TCGA-DD-A73E-01 | D32V |
| TCGA-MI-A75H-01 | D32V |
| TCGA-RC-A6M4-01 | D32V |
| TCGA-CC-A7IK-01 | D32V |
| TCGA-CC-A7IL-01 | D32V |
| TCGA-DD-A4NF-01 | D32Y |
| TCGA-G3-AAV3-01 | D32Y |
| TCGA-DD-AAW2-01 | E54D,T41A |
| TCGA-EP-A3RK-01 | G34E |
| TCGA-ZS-A9CG-01 | G34R |
| TCGA-DD-AAC8-01 | G34R |
| TCGA-DD-A119-01 | G34V |
| TCGA-G3-A3CJ-01 | G34V |
| TCGA-CC-A9FW-01 | G34V |
| TCGA-DD-A1EL-01 | H36P |
| TCGA-DD-A4NI-01 | H36P |
| TCGA-DD-AACD-01 | H36P |
| TCGA-G3-A3CK-01 | H36P,S33P |
| TCGA-ZP-A9D4-01 | I35S |
| TCGA-DD-AACX-01 | |

FIG. 4A

| Sample | Mutation |
|---|---|
| TCGA-A5-A0GW-01 | S33F |
| TCGA-D1-A0ZU-01 | S33F |
| TCGA-D1-A17C-01 | S33F |
| TCGA-AP-A0LN-01 | S33Y |
| TCGA-B5-A0K7-01 | S33Y |
| TCGA-B5-A0JT-01 | S33Y |
| TCGA-D1-A165-01 | S33Y |
| TCGA-AP-A0LG-01 | S37A |
| TCGA-B5-A11V-01 | S37A |
| TCGA-BS-A0V7-01 | S37A |
| TCGA-AP-A0LJ-01 | S37C |
| TCGA-B5-A0K0-01 | S37C |
| TCGA-BG-A0LW-01 | S37C |
| TCGA-AX-A0IS-01 | S37C |
| TCGA-D1-A15Z-01 | S37C |
| TCGA-D1-A17T-01 | S37C |
| TCGA-BG-A0M3-01 | S37C,S646F |
| TCGA-A5-A0GM-01 | S37F |
| TCGA-BG-A0MG-01 | S37F |
| TCGA-BG-A0VT-01 | S37F |
| TCGA-D1-A0ZQ-01 | S37F |
| TCGA-D1-A16B-01 | S37F |
| TCGA-D1-A16Q-01 | S37F |
| TCGA-D1-A17R-01 | S37F |
| TCGA-BG-A0MI-01 | S37P |
| TCGA-AP-A0LE-01 | S37P |
| TCGA-B5-A121-01 | S45C |
| TCGA-BS-A0TG-01 | S45F |
| TCGA-B5-A11Z-01 | T41A |
| TCGA-A5-A0GI-01 | T41I |
| TCGA-BS-A0UJ-01 | T41I |
| TCGA-B5-A11U-01 | T41I |
| TCGA-DD-AAVP-01 | I35S |
| TCGA-EP-A12J-01 | S33A |
| TCGA-FV-A4ZQ-01 | S33C |
| TCGA-ED-A7XP-01 | S33C |
| TCGA-G3-AAV4-01 | S33C |
| TCGA-DD-AAE3-01 | S33C |
| TCGA-DD-AAVX-01 | S33C |
| TCGA-XR-A8TF-01 | S33F |
| TCGA-DD-AACA-01 | S33F |
| TCGA-DD-A116-01 | S33P |
| TCGA-DD-A39V-01 | S33P |
| TCGA-G3-A6UC-01 | S33P |
| TCGA-DD-AADE-01 | S33P,S45Y |
| TCGA-CC-A5UD-01 | S33Y |
| TCGA-DD-AADD-01 | S33Y |
| TCGA-KR-A7K0-01 | S37A |
| TCGA-DD-AAEK-01 | S37A |
| TCGA-UB-A7MC-01 | S37C |
| TCGA-DD-AADG-01 | S37C |
| TCGA-BW-A5NQ-01 | S37F |
| TCGA-5C-A9VG-01 | S37F |
| TCGA-DD-AAD0-01 | S37Y |
| TCGA-4R-AA8I-01 | S45F |
| TCGA-LG-A9QD-01 | S45F |
| TCGA-ZP-A9CV-01 | S45F |
| TCGA-3K-AAZ8-01 | S45F |
| TCGA-BC-A10U-01 | S45F,S45Ffs*5 |
| TCGA-O8-A75V-01 | S45P |
| TCGA-RG-A7D4-01 | S45P |
| TCGA-NI-A8LF-01 | S45P |
| TCGA-G3-AAV2-01 | S45P |
| TCGA-G3-AAV6-01 | S45P |

FIG. 4B

| | |
|---|---|
| TCGA-BG-A187-01 | T41I |
| TCGA-AP-A059-01 | V199I |
| TCGA-B5-A0V8-01 | K170M |
| TCGA-B5-A11E-01 | K354T |
| TCGA-AP-A054-01 | M688T |
| TCGA-AP-A0LM-01 | R535Q |
| TCGA-AP-A056-01 | R587Q,D712N |
| TCGA-AX-A0J1-01 | R710H |
| TCGA-D1 A103-01 | A215T |

| | |
|---|---|
| TCGA-2Y-A9H1-01 | S45P |
| TCGA-WX-AA47-01 | S45P |
| TCGA-DD-AAEE-01 | S45P |
| TCGA-DD-AAEH-01 | S45P |
| TCGA-DD-AAVQ-01 | S45P |
| TCGA-DD-AAW3-01 | S45P |
| TCGA-DD-A4NK-01 | S45Y |
| TCGA-5R-AA1C-01 | S45Y |
| TCGA-DD-A11D-01 | T41A |
| TCGA-2Y-A9HB-01 | T41A |
| TCGA-DD-AACJ-01 | T41A |
| TCGA-DD-AADU-01 | T41A |
| TCGA-DD-AAE9-01 | T41A |
| TCGA-EP-A26S-01 | T41I |
| TCGA-2Y-A9HA-01 | T41I |
| TCGA-CC-A7IH-01 | T42_K49del |
| TCGA-DD-A1EA-01 | L31_I35del |
| TCGA-DD-A1ED-01 | V136A |
| TCGA-CC-5262-01 | W383C |
| TCGA-G3-A5SJ-01 | Y333F |
| TCGA-DD-A39Y-01 | K181Rfs*28 |
| TCGA-DD-A1EJ-01 | K335I |
| TCGA-DD-A3A4-01 | K335I |
| TCGA-DD-A4NL-01 | K335I |
| TCGA-MI-A75C-01 | K335I |
| TCGA-DD-AACK-01 | K335I |
| TCGA-K7-A6G5-01 | K335T |
| TCGA-DD-A39W-01 | L139F |
| TCGA-G3-A25Z-01 | L405F |
| TCGA-DD-A1EE-01 | L405F,K335I |
| TCGA-DD-A73A-01 | N387I |
| TCGA-EP-A3JL-01 | N387K |

FIG. 4C

SEQUENCE LISTING

<160> NUMBER OF SEQ ID NOS: 27

<210> SEQ ID NO 1
<211> LENGTH: 15274
<212> TYPE: DNA
<213> ORGANISM: Homo sapiens

<400> SEQUENCE: 1
atggctactc aaggtttgtg tcattaaatc tttagttact gaattggggc tctgcttcgt 60
tgccattaag ccagtctggc tgagatcccc ctgctttcct ctctccctgc ttacttgtca 120
ggctaccttt tgctccattt tctgctcact cctcctaatg gcttggtgaa atagcaaaca 180
agccaccagc aggaatctag tctggatgac tgcttctgga gcctggatgc agtaccattc 240
ttccactgat tcagtgagta actgttaggt ggttccctaa gggattaggt atttcatcac 300
tgagctaacc ctggctatca ttctgctttt cttggctgtc tttcagattt gactttattt 360
ctaaaaatat ttcaatgggt catatcacag attctttttt tttaaattaa agtaacattt 420

```
ccaatctact aatgctaata ctgtttcgta tttatagctg atttgatgga gttggacatg    480
gccatggaac cagacagaaa agcggctgtt agtcactggc agcaacagtc ttacctggac    540
tctggaatcc attctggtgc cactaccaca gctccttctc tgagtggtaa aggcaatcct    600
gaggaagagg atgtggatac ctcccaagtc ctgtatgagt gggaacaggg attttctcag    660
tccttcactc aagaacaagt agctggtaag agtattattt ttcattgcct tactgaaagt    720
cagaatgcag ttttgagaac taaaaagtta gtgtataata gtttaaataa aatgttgtgg    780
tgaagaaaag agagtaatag caatgtcact tttaccattt aggatagcaa atacttaggt    840
aaatgctgaa ctgtggatag tgagtgttga attaaccttt tccagatatt gatggacagt    900
atgcaatgac tcgagctcag agggtacgag ctgctatgtt ccctgagaca ttagatgagg    960
gcatgcagat cccatctaca cagtttgatg ctgctcatcc cactaatgtc cagcgtttgg   1020
ctgaaccatc acagatgctg aaacatgcag ttgtaaactt gattaactat caagatgatg   1080
cagaacttgc cacacgtgca atccctgaac tgacaaaact gctaaatgac gaggaccagg   1140
taagcaatga catagctagc tttttagtct gctttgaagt aaatgctcaa ggggagtagt   1200
ttcagaatgt ctacccaata ccagtacttg aaaactaacg atgtttctga attcctgtat   1260
tacaggtggt ggttaataag gctgcagtta tggtccatca gctttctaaa aaggaagctt   1320
ccagacacgc tatcatgcgt tctcctcaga tggtgtctgc tattgtacgt accatgcaga   1380
atacaaatga tgtagaaaca gctcgttgta ccgctgggac cttgcataac ctttcccatc   1440
atcgtgaggg cttactggcc atctttaagt ctggaggcat tcctgccctg gtgaaaatgc   1500
ttgggtaaga aaacatgtca gaatgcttga agctaaaaag tagaagagta tactcacaat   1560
atttctgatg aggctttttt cttcttccca gttcaccagt ggattctgtg ttgttttatg   1620
ccattacaac tctccacaac cttttattac atcaagaagg agctaaaatg gcagtgcgtt   1680
tagctggtgg gctgcagaaa atggttgcct tgctcaacaa aacaaatgtt aaattcttgg   1740
ctattacgac agactgcctt caaattttag cttatggcaa ccaagaaagc aaggtaagag   1800
aattattctt tatgtggttt tcatggagca ttggacacct ccagtgtcat gtcattccat   1860
gcagtgttcc taaccttttt ggcaccaggg accagtttcg tggaaaacag tttttccatg   1920
aatgggttgt gggaatggtt tctggatgac accattccac ctcagataat caggcattag   1980
attctcatag ggagcgtgca gcctagatcc ctcgcatgtg cagtccacac tagggtttct   2040
actcctatga gactctcatg gtgcagttga tctgacagga ggtagagctc aagccaggta   2100
atgctcgctc acctgccact tacctcctgc tgtgcagccc agttcatttc tgttctttta   2160
aatttttgag tttccatatg taaagcacta tgcgaagtag tagggatatg gtaggcaagc   2220
ttctcttcac actttttgttc ttaggtggga tgtagatgtt gggaataata acctaatatt   2280
taatttgtgt agtgggaaga agtggggcta tgagggcaca taacacaagt tgaaactgac   2340
tctttttgag ggttcaagga gacctcttgg aggaagtgat agttgagttc agtgttcaag   2400
gatgagaagg gattcactag gtgaaggtta ggtgagaaaa caacatcttt gaaacgaagg   2460
aaggagatgg aaagttttgg gaatttaaga aatactaata gtaaggagga agaaaggttt   2520
gaggtgaggc tattgagata gacttagcag atctcatagg gctttgtaga gcatgtttaa   2580
aagcacaatg ggaaatttca gcagaagcct gaaatgatga aatttgtttt tagaaaattg   2640
gggcagtgtt gaaagggaag atatacaggg aatgaaagga caagcatgaa tgatcatttt   2700
atggtatctg tttttaaggt ggatataatt aggaaaatta aagggccaaa tgatgaggag   2760
```

-continued

```
ttaagtgcca gttctggttc aaattttcag tgaatcagtt ttgatataac tttcatctta   2820
gggcattact cttgcctacc aacatagttt ctaaattttt ttcttttggt gtgatcactg   2880
tgggaagaag gaaattgggc ccaaactgat acattgtttg gaggactggg atgtctgaat   2940
ttgagtggaa tgctttaaaa ggacaagttg gatagggccc cagtatgggg gtctgagtga   3000
tggggtccag gaatacattt aggtccaatg gcaagctggc tgaaattctt gtataataaa   3060
ataggttggt aatatggctc ttctcagaca tgtgatcaag attccttgac taacaagata   3120
tatatatata tctttctagc tcatcatact ggctagtggt ggaccccaag ctttagtaaa   3180
tataatgagg acctatactt acgaaaaact actgtggacc acaagcagag tgctgaaggt   3240
gctatctgtc tgctctagta ataagccggc tattgtagaa gctggtaagt atatgtatct   3300
attctgagtc ttgtgtatag catctgcagt tctaattaga ttacttttct taggaaaagg   3360
tggtagaact ttaactactg aaaataaatg gtcctattca gtttgcagcc aagatttaca   3420
ttcagagtac ctgtcatctg gattgtagct aaatatttaa ggctagttta ggtagagttc   3480
ttattatcca tcaaaaatga tggcatatgt tttgcttaat aaaatttgtt tgtaatttca   3540
gttttgagta aacctaagat ttgctaacag agctgtgaat ttataggaga aaagacaaat   3600
tctaatatag tacagtttta tgtaaagtga ttgctttatt agtagatgct catgagcagt   3660
ttttgttttg ttttaacttt taggttccgg gtaatgtgca ggcttgttat ataggtaaat   3720
tgcatgtcac aggggtttcg tgtgcagatt attttgtcac ccaggcagta agtattgtac   3780
ccaataggta gtttttcagt tctttacctc ccacccgtaa gtaggcccca gtgtctgttg   3840
ttcccttctt tgtgcccgtg tgtactcagt gtttacctcc cacttataag tgagaacatg   3900
tggtatttgg ttttctattc ctatgttagt ttgcttagga taatggcctc cagctccatc   3960
catgttgctg aggaagacat cttggtattt ttttatggct gcttagtatt ccatagtata   4020
tatgtaccac attttcttta tctagtctac cattgatggg catttaggtt aattccatat   4080
ctttgctatt gtgaataatg ctgcagtgaa catatgcatg catgtgtctt tatggtaaaa   4140
agatttcttt ttctttgggc atatacctaa taataggatt gctggattga atggtaattc   4200
tgtcaggttt tttgagaaat caccaaattg ctttccacaa tggctgaact aatttacttt   4260
cccaccagca gtgtataagc attctctttt ctcagcaacc tcaccagcat ctgtcatttt   4320
ttgacttttt attagtagcc attctaactg gtgtgagacg gtatctcatt gtggttttga   4380
tttgcatttc tctaatgatc agtgatgtcg agcttttctt catatgtttc ttggccactt   4440
gtatgtcttc ttttgaaaag tgtctgttca tgtcctttgc ccacttttta atggggttgt   4500
tctttttttgc ttgttaattt aagtttattg taaactctgg atattagacc tttgtcagat   4560
gcatagtttg ccagtacttt ctcccatgcc agtactttct cccattctgt aggttgtctg   4620
tttactctgt tgatttcttt tgctgcgcag aagctcttta tactgtccca tttgtcagtt   4680
tttgtttttg ttgcaacttc tcttggcatc ttcgtcatga aatctttgcc aggtcttatg   4740
tccagaatgg tatttcctag gttatcttgc agagttttta cagttttaag ttttatattt   4800
aagtctttaa tccattctga gttgattttt gtacatcatg taaggatggg gtgcagtttc   4860
aatcttggat gtggctagcc agttatccca gcaccattta ttgaataggg agtcctttcc   4920
ccattgcttg tttttgttta cttgttaggt gtgcggccta acttctgggc tttcttttct   4980
gttccattgg tctctgtgtc tgtttgtata ccagtaccat gctgtgattg taaccttgta   5040
ttaacagtat agcttgaagt tgggtaaagt gattcctcca gttttgttct tttgcttag    5100
gattgccttg gctattcagg ctcttttttg ggttcatatg aatttttaaa tagttttttt   5160
```

```
ttaattatgt gaagaatgcc attggtagtt tggtaggaat agcattgaat ctgtgaattg   5220
ctttgggctg tatggccatt ttaacaatat tgattcttcc tgccatgaaa tagaatgttt   5280
tttcatttgt tggtgtcatc tctgatttct ttgagcagtg ttttttgtaa ttctcattgt   5340
agagatcttt cacctccctg gttagttgta ttcctaggta ttttattctt tttgtggctt   5400
tggtaaatgg gattgcattc ttgatttggc ttgcagcttg gatgttgttg gtgtctagaa   5460
atgcttctga cttttgtaca ttgattttta tatcctgaaa ctttgctgaa gtttattgga   5520
tcaaggagct tttgggcaga gattatgggg ttttctaggt atagaatcat attgtttgca   5580
aacagacttc ctatttggat gcattttctt tctcttgcct gattatgagc agtgttttgc   5640
cctgatattc tgtattctca gtgaatagat gtcgtctaag tatgagaaac aatttttttc   5700
tattctgagt atttttaaga aggcaactta tatgtggtac tttgtatatt gtgtatgttg   5760
gcaattgggg aaaagaatag atggtttgta ctagggcctc ttgggttctg tgtgtgtgtg   5820
tgtgtgtgtg tgtgtgtgtc atgaaaacag ttacttttta gctaccaagc atttttttctc  5880
ctttcagtaa cccacctaac aacatttact cagaatttca aagcaagctt caaatcagta   5940
ttgaaagaag gaaaaatata aaggcattta atggaagaaa atgttgggaa taaagtatag   6000
ggctggcaac acttactttt ctcacttatt gagagtaatt ttacttggga atttatgaga   6060
gagaaagaca ttatgattgc tccaggtaac tactggcaga ggaaccatag tcttggggat   6120
agacaaatgt ggctgagttc atatagaatg aggggatggg atgtaaattc tgtcagctgt   6180
tccagcagta acctgtaatg taggctaaaa atacagattt tgagatttat ttaatcagaa   6240
tccctggagt gttaattttt atatcaagat ctcatagtgt tttatttgaa gtgacaggga   6300
ggtctgtaga tagctggaca tgtatgggac tggaagctta ggaatcttta agttcttcca   6360
ggttattctt atgttcattt gtttattctg aaaatagcat ctaatgtatt ttaagaaatg   6420
gaataggcac atagtataca ttgggtaaca caacagatag ggtccccgtg cttaattctt   6480
agtcttgtga aggtgacaaa aatacttaaa aatatgtgat cctaaattag aatgagtgtt   6540
atgggagaaa tgacagcaaa tagtgatgag aattaatggg gaggggaatt gtctagatga   6600
gagggaaaag gtctccttga aaaggggatg ttaagtggga ctgcaggatg agagggaacc   6660
gtctcttgtc tatatgagaa gtgagggtta aacgttttcc aggtagagaa aaggaacacc   6720
atgtgctatg tcttagaacc agggatatcc agtcttttgg cttccctggg ccacattgga   6780
agaagaataa ttgtcttggg ctacacacca aatacactaa tgatagctga tgagctaaaa   6840
caaaaaaaaa ttgcaaaaga atctcataat gtttaagaaa gtttacgaat ttgtgttggg   6900
ctacattcag agctgtccta ggccatgtgg cccatgggct gcaggttgga caagcttgcc   6960
ttagaaggaa agagattggt caggcacggt ggctcacgcc tgtaattcca gcactttggg   7020
aggctgaggt gggcggatca tgaggtcagg agatcgagac cagcctggct aacacagtga   7080
aaccccatct ctactaaaaa tacaaaaagt tagccgggcg tggtggcagg cgcctgtagt   7140
cccagctact tgggaggctg aggcaggaga atggtgtgaa cccgggaggc ggagcttgca   7200
gtgagctgag atagcgccac tgcacttcag cctgggcgac agagtgagac tctatctcaa   7260
aaaaaaaaaa aagggaaaga gattgtggag atccaggtgc tgaagagaag gtctgcataa   7320
acagaactta gtaatgaggt ggatggcctg gtatgaggtt gaggttaggt aagcagagcc   7380
ataacatgca ggactttcta ggttcctata agatagttac tactcatgga gtttattcat   7440
gctttattcc agctttggag ccatagatac agaatacttt ggtcagtttg gaaggctagg   7500
```

-continued

```
tgggatccaa attctaaacg gttcctcagg gttatactaa agtatttcta ttatcttaaa   7560
aggatgctga gacactttcg atggttgttt atcaatagca aagcatcaca gtggtgtgtt   7620
taaaatatta ataatagcat tgtatagatt aacagtttga atgaccaaaa gctagaagac   7680
cagactactg agatgttaca ggcttttagg aatgaaatag tttgctttta gaactcaata   7740
gcaaagggca gatgtctgag atgcctgaaa gaatcataga atgtaataat ataggagcta   7800
agggagcaac caaaaacggt ttgtggaggg gacaacattg gtaccatgaa gataaatgga   7860
accctcagaa ggcatcctta atttttgaac ataataattt aagaagctga cttaaagtga   7920
cttaaaaggt cagtaggtag ctggaaatgt atgatactag aatgcaagag aggcaggcta   7980
gagatttgga agtttccctc ttagtatata ggggtaaggg cagcagggaa ggggaggtag   8040
aggtgccaca gagtcatctg tatgggactt tttttttac cctagaactg ctgaatcaga   8100
atgtgtgtgt tttaaagtct ctgtaggcca ttctgatgga catctggggt taaaatccat   8160
tctcttagag ttaatagtta tgtaaaggga gggaatgaag tcttaaagag gggaaagaag   8220
gtagtcattt cacaaatact gagcatcctg atcatcagtc ttacgcagat cattctatta   8280
gtagctggag ctactatgaa aaaggaaccc aacagaggtg atctttgtct tgtagggaaa   8340
gtggagtaac ttacactatg aaggagaagt gcagggtacc ataagaatta cagcagatag   8400
acctcatctg aggaaataaa acagacccga aagatgaagg agacaaggaa aagtatctct   8460
tactgcattc agaagtgatt taagttgaag atggatgagc gaagttaatc tactatgtgg   8520
gcattgggct tccatttata ctcctttgcc agagtaaatg tcccccattt aagggtccta   8580
aaggatggaa gattgtaaac cttggaacac atgttttgta gtcagtgaat tgtataaagt   8640
ccctgacagt aagtgttttc atgccgtctt tctggattgt tcttacccca ggaatttacc   8700
tagcttcttt aggtctttag tcagatgtca ccttcacagt gaggtgacct aattatctat   8760
ttaaaatcgc agccccactc cattattttt ctccatagcc ctttaatatc atctgacata   8820
ctgtatggtt ttagtttatt gtatattttt ctgcctcttc caactagatc ataaattctg   8880
agggtaggaa cttctgaata tttttgttca ctggtctatc tgcagctcag aacaggacct   8940
ggtactgaat aaatattttt gaaatgattg aatggatgaa aagaaatgag taataagaat   9000
attacctaag ggggacagtg gagataacaa aggctttttc ggcttaggaa aggaacagta   9060
gctatttgag agtttgtcac tagtgaggtg aactggcaaa gtgaaggaaa ctgagcaaca   9120
ttctagaaaa tgagaggaaa tcaaatactt aggtgaaagg aagtaaactc tggaaataca   9180
gaaggacacc tcctaaggct agaacagata tttaggattg ataggcactt ctagctaatg   9240
actagggcct tatatccttt ttaattttct aggtggaatg caagctttag gacttcacct   9300
gacagatcca agtcaacgtc ttgttcagaa ctgtctttgg actctcagga atctttcaga   9360
tgctgcaact aaacaggtaa attctgagta aactggtgcc atgggaatag agtcaagatg   9420
agtatgtgct tgtactgacc atctgttttt atctccatag gaagggatgg aaggtctcct   9480
tgggactctt gttcagcttc tgggttcaga tgatataaat gtggtcacct gtgcagctgg   9540
aattctttct aacctcactt gcaataatta taagaacaag atgatggtct gccaagtggg   9600
tggtatagag gctcttgtgc gtactgtcct tcgggctggt gacagggaag acatcactga   9660
gcctgccatc tgtgctcttc gtcatctgac cagccgacac caagaagcag agatggccca   9720
gaatgcagtt cgccttcact atggactacc agttgtggtt aagctcttac acccaccatc   9780
ccactggcct ctgataaagg taaattgtca aagtagaatt tacctttgtt gcagaattga   9840
aaatgaagca tctctagctg ttggatggct gtctaagcat agtgatcaat aagtaggaat   9900
```

```
tgtattcctt agtaagtagg aagtatggct gcgatagggg taagattctg aaatgtttgt   9960
gtagtcagaa ctacttttag ttgataccaa tagatttagt gtggtgggaa ttttagggta  10020
agaaaatgat tttgttgagt tgtatgccag ttcttccttc tgtttttcag gctactgttg  10080
gattgattcg aaatcttgcc ctttgtcccg caaatcatgc acctttgcgt gagcagggtg  10140
ccattccacg actagttcag ttgcttgttc gtgcacatca ggatacccag cgccgtacgt  10200
ccatgggtgg gacacagcag caatttgtgg taggtaaatt cttacagtga tacctggcta  10260
tctaaaagga atgcataaat ccaaaggatc ctgaacttct ttctttggtc attggttccc  10320
cccatccgtc ttcctgaaga gctaatgaca aagtaaataa ataaataatt acacatttct  10380
atggctgcag agaaaataag gcatagtgtg gccccagtga tatttccttg gacacgtcct  10440
tcacatggtc agtcttacaa aggttgggtt aggtgtttca taaagtgttc tcatttaatt  10500
tacacaaagg cccacttcct taggaagagg tagagtcata atttgagatc aaatctgtgt  10560
aatttcagag cctcttaccc ttgcctcatc atgcattttg actataaata tttagcagtc  10620
cgttttatta tcttttctgt gagttaaact tttttcatgg acctaagaat attcagaaat  10680
aagtagtagc atttctgtac tcttaaccac aaaaatctca acctgaagct ttgatacaaa  10740
gtttgtgtct taaaagtagc ttcattaaaa gtatagtcta atgacatttc tgatttctca  10800
gactttaaga ccttattagg ttagtttaga aaacaaagat ggagcctacc agaacagatg  10860
ttaggaatct cattttgctg gttgctttgt gtatgtactc atattggggc tttggctttc  10920
ttcatttatt actgttggta ttggcccatc tccatgaggt gacttaatag aacgttgagg  10980
gcacctttta ttttaaatct cttttctagg aagaagagag tttttgtgtc cttgtaagaa  11040
tcaagttatt tataaaagct gctaaatgta gcagaataat aaccccttttt aaaactcaaa  11100
tccagaaaca ggagaaacag atggtactta catattgcaa aagctatctt ccttctatac  11160
atgaggctgt cagctgaata gtcttggaag agtgaggagt gaatttttct gctggcaact  11220
cggttagttt tagcagttgg tgctaaaact tggcaaagtt ttcaccaaat acatggaaga  11280
tatacaaaaa tagagggggc atgtaaaaga aaaacgttga catagtctga gcattacttt  11340
ctcatcttct ctttttatat accttttacc cagaatgatt ggtgccctta ctgtaggaaa  11400
gttgtctttg ggattcagcg ctgtatggaa gctctgttgc actgtgtatg ggggaggggt  11460
gctgctttga attagtgctg ccaggaggcc tcttttcagt gacattcaag ttaatggaat  11520
ccttcttcct tcctgaacta attgcaagtt acggggaact tcgggtatat aatgtaaata  11580
attacagtct aataattgtt cctcaaactt tacagaggag aatgccctgt ttgttaacca  11640
tgtttctttt ggcaggaggg ggtccgcatg gaagaaatag ttgaaggttg taccggagcc  11700
cttcacatcc tagctcggga tgttcacaac cgaattgtta tcagaggact aaataccatt  11760
ccattgtttg tgcaggtatg ttttaagtga agtgttctag gttttatgtc cataaaattt  11820
ccagattgta atgactaata acatttcaga aaattaggga ccataatagg gttaccaaca  11880
tttaatttta tgaaaattcc ctacattttt tggtcagtaa gagaaacatt gagacttgag  11940
aagagggagg agatttcaca tttcactttt atgggtgcct agaggggaga gctgacctgg  12000
gctgccagag gcagggcata gacccccaac caattctggg ttttccaaat cttagatcag  12060
ttagagctgc ctctgaagaa agggtttata gctaaaaaat attatggaaa tccagtgctc  12120
cagagcatta aacaccccaa gacataaaat tcagagaata ttatttacta cagtgtgaat  12180
gcctcttgca ctctgaattg ggaatgtttg caccacagtg gggggcttgc catgttttag  12240
```

```
ctttagattt aattaggttt tgtttgtgtt ttctccttag ctgctttatt ctcccattga  12300
aaacatccaa agagtagctg caggggtcct ctgtgaactt gctcaggaca aggaagctgc  12360
agaagctatt gaagctgagg gagccacagc tcctctgaca gagttacttc actctaggaa  12420
tgaaggtgtg ggtaagtaaa aaggaaccaa agcctttagc agatgtgtac attgaagtct  12480
cagtttttcc tcaagggcct ttttctcctt gtctcttagc gacatatgca gctgctgttt  12540
tgttccgaat gtctgaggac aagccacaag attacaagaa acggctttca gttgagctga  12600
ccagctctct cttcagaaca gagccaatgg cttggaatga ggtagggaaa tgtgagcagt  12660
tatttatctg gtagtttcct agagcaggta tggcagcttg ttctttcctc tcaaaacact  12720
tagtacacat tcatttgcat tgatgtttcc ctggcttgag tatttcttct ttatgctgtc  12780
tagcaactgc tctgaggaag aactataata caagctttaa agagtctgtt cagaatcatt  12840
acaaataagt tgtgttattt aaaattataa ttcataaggg agaaagatga aaaatgttac  12900
cagattaaag aagatttttc aaaaggatgt aaggaaagag gcagtgttaa acactgttaa  12960
gaggacagtt tatcagtatt ttttactaaa ctttaataaa acttttctat ttgaatttct  13020
gctatgaatt tttcttcagc atttgtcctc agtacaggtg gttccttgaa acattgtttc  13080
taataaaact agaacatcct gatattttat ccattctata gagatcattg atggtacaca  13140
gacatacagt ggattatgtt tgttgagtga atggaaagag agattgttag gtttacaacg  13200
atgcagctct tgagaccgga gtttaagatc agcctgggca acatagtgaa accccatctt  13260
tagctgggca tggagatgga tgcctatagt cctagctact ggggagacgg gggcaggagg  13320
attgcttgaa cccaggagtt aacagactgc actcagtgac agagccagac tccaacacaa  13380
aaaaaaaaaa aaaaaaaaag caaattacca gtgagtagtg tgttacttgg gtttttaata  13440
ggcatcttat taacatgttc caacttgagc ccttaacttt ctccacctac ccccttccac  13500
aaacctgttt tcactgtctt ctctgtctta gttaatgtca gctttgtctg tccagctgct  13560
caggctaaaa cttttctttc atataacaca tcctatcagc agctcctgtt tgtgggtagg  13620
cattttgcct tttttttttt tttttttttt aaactgctat atctctagca tgtagaacag  13680
tgcctggcag cacataatag gtgcttaata taatatttgt tgaaagaaca agtcagtgag  13740
tatttttaat gtgaggtgca aagagaaaaa aaaatgtatc tttgaggtgt ggagttttga  13800
agaacttcca ttttctaagc atttgtgtaa tgttggagtt acttgttcct tttgtaatct  13860
gaaagtatgc tttaaaaaaa attagtgtac ttttgagaat tttcattttg ctttctattc  13920
ttccttgctt tgtgcatgtt tatctagact gctgatcttg gacttgatat tggtgcccag  13980
ggagaacccc ttggatatcg ccaggatggt atgtgtctca tatttctcga ttaactccag  14040
atcaagctaa agttctaaaa cttttatcag aagagccggt ttgctcatct gggaaaccag  14100
tgttggcaga aaagtagtgg cttcaattaa aagcagttct taaattccag tcagcaacag  14160
tatctttaat ggagcacagg gaattcagag ccacacaatg agtagcagta ggattacacc  14220
accaacaaat acatgctact gctaggcctc tgcagtgcag gatgttacaa tttacctggc  14280
tttttattct ctttttggcc agaggactca taatacttt gtctacaagc tacccaagga  14340
agataggaaa actcctgttt ctaggctcag atctcgggtg ggtttttaca tagttgcatt  14400
atcatcaggg ttttcttgaa aagctaattt aaatctgggt aatgaacatg gaggatggca  14460
tagaccacta acaattataa ctgtcttaca tttataaccg catctgcttc tacctaatta  14520
tgaaaccact aaagcgcaga ttcttactgt gagaaataac atgtcaaccc taagataaaa  14580
tatgttgagg tttcatggaa atagtgcctt tccttagtac ttttgtgggt gtcacttggc  14640
```

```
cttttgtca agatagatta cacctgccag acctcattat tgtcttaatc ctccttccca  14700

tgacttctca ctgcctaggt ggtcacacag tagattcctg cttcttctcc tcgggaaccc  14760

caagtctctt gacaggggta aatgcagagt gttcagggtt agactaatga tgtgactagg  14820

ccctgctggt gtgcctgtct gatggaaata gatgttattt gtgtagtctc atgggtggcc  14880

tggcactgag taattacttg gctaaagaaa gctggaggtt gaagaggcta gaaagcgttg  14940

ttttctgaca agtttgctgc tgaactttgg atgccctaac ctcagtgtta acgtctatgt  15000

ctgcttctct cctctctctt ttgccttcct tcttgcctat tttgttgaca ccctgactct  15060

tctagatcct agctatcgtt cttttcactc tggtggatat ggccaggatg ccttgggtat  15120

ggaccccatg atggaacatg agatgggtgg ccaccaccct ggtgctgact atccagttga  15180

tgggctgcca gatctggggc atgcccagga cctcatggat gggctgcctc caggtgacag  15240

caatcagctg gcctggtttg atactgacct gtaa                              15274
```

<210> SEQ ID NO 2
<211> LENGTH: 781
<212> TYPE: PRT
<213> ORGANISM: Homo sapiens

<400> SEQUENCE: 2

```
Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255
```

```
Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
```

```
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780


<210> SEQ ID NO 3
<211> LENGTH: 4
<212> TYPE: PRT
<213> ORGANISM: Homo sapiens

<400> SEQUENCE: 3

Met Ala Thr Gln
1


<210> SEQ ID NO 4
<211> LENGTH: 77
<212> TYPE: PRT
<213> ORGANISM: Homo sapiens

<400> SEQUENCE: 4

Ala Asp Leu Met Glu Leu Asp Met Ala Met Glu Pro Asp Arg Lys Ala
1               5                   10                  15

Ala Val Ser His Trp Gln Gln Gln Ser Tyr Leu Asp Ser Gly Ile His
            20                  25                  30

Ser Gly Ala Thr Thr Thr Ala Pro Ser Leu Ser Gly Lys Gly Asn Pro
        35                  40                  45

Glu Glu Glu Asp Val Asp Thr Ser Gln Val Leu Tyr Glu Trp Glu Gln
    50                  55                  60

Gly Phe Ser Gln Ser Phe Thr Gln Glu Gln Val Ala Asp
65                  70                  75


<210> SEQ ID NO 5
<211> LENGTH: 84
<212> TYPE: PRT
<213> ORGANISM: Homo sapiens

<400> SEQUENCE: 5

Ile Asp Gly Gln Tyr Ala Met Thr Arg Ala Gln Arg Val Arg Ala Ala
1               5                   10                  15

Met Phe Pro Glu Thr Leu Asp Glu Gly Met Gln Ile Pro Ser Thr Gln
            20                  25                  30

Phe Asp Ala Ala His Pro Thr Asn Val Gln Arg Leu Ala Glu Pro Ser
        35                  40                  45

Gln Met Leu Lys His Ala Val Val Asn Leu Ile Asn Tyr Gln Asp Asp
    50                  55                  60

Ala Glu Leu Ala Thr Arg Ala Ile Pro Glu Leu Thr Lys Leu Leu Asn
65                  70                  75                  80

Asp Glu Asp Gln
```

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

His Ala Ser Asp Ser Ile Ser Asn Ser Leu His
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ala"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: MISC_FEATURE
<222> LOCATION: (1)..(7)
<223> OTHER INFORMATION: /note="Variant residues given in the sequence have no preference with respect to those in the annotations for variant positions"

<400> SEQUENCE: 7

Tyr Gly Arg Gln Ser Ile Gln
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="Ala"
<220> FEATURE:
<221> NAME/KEY: MISC_FEATURE
<222> LOCATION: (1)..(9)
<223> OTHER INFORMATION: /note="Variant residues given in the sequence have no preference with respect to those in the annotations for variant positions"

<400> SEQUENCE: 8

Gln Gln Ser Glu Ser Trp Pro Leu His
1               5

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 9

Gly Phe Thr Phe Ser Ser Tyr Thr Met Ser
1               5                   10


<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Ile Ser Gly Gly Gly Phe Gly Thr Tyr Tyr Pro Asp Ser Val Lys
1               5                   10                  15


<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Asn"
<220> FEATURE:
<221> NAME/KEY: MISC_FEATURE
<222> LOCATION: (1)..(10)
<223> OTHER INFORMATION: /note="Variant residues given in the sequence
      have no preference with respect to those in the annotations
      for variant positions"

<400> SEQUENCE: 11

Pro Gly Tyr His Asn Tyr Tyr Phe Asp Ile
1               5                   10


<210> SEQ ID NO 12
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (51)..(51)
<223> OTHER INFORMATION: /replace="Ala"
<220> FEATURE:
<221> NAME/KEY: VARIANT
<222> LOCATION: (55)..(55)
<223> OTHER INFORMATION: /replace="Glu"
<220> FEATURE:
<221> NAME/KEY: VARIANT
<222> LOCATION: (92)..(92)
<223> OTHER INFORMATION: /replace="Ala"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
```

```
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys
            100                 105


<210> SEQ ID NO 13
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (102)..(102)
<223> OTHER INFORMATION: /replace="Asn"
<220> FEATURE:
<221> NAME/KEY: MISC_FEATURE
<222> LOCATION: (1)..(119)
<223> OTHER INFORMATION: /note="Variant residues given in the sequence
      have no preference with respect to those in the annotations
      for variant positions"

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr His Asn Tyr Tyr Phe Asp Ile Trp Gly Gln Gly
            100                 105                 110

Thr Thr Val Thr Val Ser Ser
        115


<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
```

```
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys
            100                 105


<210> SEQ ID NO 15
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr His Asn Tyr Tyr Phe Asp Ile Trp Gly Gln Gly
            100                 105                 110

Thr Thr Val Thr Val Ser Ser
        115


<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Ala Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Ser Glu Ser Trp Pro Leu
                85                  90                  95

His Phe Gly Gly Gly Thr Lys Val Glu Ile Lys
            100                 105


<210> SEQ ID NO 17
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Asn Asn Tyr Tyr Phe Asp Ile Trp Gly Gln Gly
            100                 105                 110

Thr Thr Val Thr Val Ser Ser
        115


<210> SEQ ID NO 18
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys
            100                 105


<210> SEQ ID NO 19
<211> LENGTH: 107
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Ala Arg Gln Ser Glu Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys
            100                 105


<210> SEQ ID NO 20
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr His Asn Tyr Tyr Phe Asp Ile Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
```

```
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445


<210> SEQ ID NO 21
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 22
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Asn Asn Tyr Tyr Phe Asp Ile Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445


<210> SEQ ID NO 23
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Ala Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 24
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr His Asn Tyr Tyr Phe Asp Ile Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285
```

```
Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445


<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Ala Arg Gln Ser Glu Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 27
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Thr Leu Asn Ser Val Leu Asn Ser Asn Ala Ile Lys Asn Leu Pro Pro
1               5                   10                  15

Pro Leu Gly Gly Ala Ala Gly His Pro Gly Ser Ala Val Ser Ala Ala
            20                  25                  30

Pro Gly Ile Leu Tyr Pro Gly Gly Asn Lys Tyr Gln Thr Ile Asp Asn
```

-continued

```
        35                  40                  45

Tyr Gln Pro Tyr Pro Cys Ala Glu Asp Glu Glu Cys Gly Thr Asp Glu
    50                  55                  60

Tyr Cys Ala Ser Pro Thr Arg Gly Gly Asp Ala Gly Val Gln Ile Cys
65                  70                  75                  80

Leu Ala Cys Arg Lys Arg Arg Lys Arg Cys Met Arg His Ala Met Cys
                85                  90                  95

Cys Pro Gly Asn Tyr Cys Lys Asn Gly Ile Cys Val Ser Ser Asp Gln
            100                 105                 110

Asn His Phe Arg Gly Glu Ile Glu Glu Thr Ile Thr Glu Ser Phe Gly
        115                 120                 125

Asn Asp His Ser Thr Leu Asp Gly Tyr Ser Arg Arg Thr Thr Leu Ser
    130                 135                 140

Ser Lys Met Tyr His Thr Lys Gly Gln Glu Gly Ser Val Cys Leu Arg
145                 150                 155                 160

Ser Ser Asp Cys Ala Ser Gly Leu Cys Cys Ala Arg His Phe Trp Ser
                165                 170                 175

Lys Ile Cys Lys Pro Val Leu Lys Glu Gly Gln Val Cys Thr Lys His
            180                 185                 190

Arg Arg Lys Gly Ser His Gly Leu Glu Ile Phe Gln Arg Cys Tyr Cys
        195                 200                 205

Gly Glu Gly Leu Ser Cys Arg Ile Gln Lys Asp His His Gln Ala Ser
    210                 215                 220

Asn Ser Ser Arg Leu His Thr Cys Gln Arg His
225                 230                 235
```

USE OF BETA-CATENIN AS A BIOMARKER FOR TREATING CANCERS USING ANTI-DKK-1 ANTIBODY

RELATED APPLICATION

This application is the U.S. National Stage of International Application No. PCTUS2017/58555, filed Oct. 26, 2017, which designates the U.S., published in English, and claims the benefit of U.S. Provisional Application No. 62/413,198, filed on Oct. 26, 2016. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: DCQ-00401 SEQ, created Apr. 25, 2019, 62 KB in size.

BACKGROUND OF THE INVENTION

Cancer remains an important public health threat with poor prognosis and limited treatment available for many types. There is a significant unmet need for therapies that can increase efficacy in treating cancers, particularly esophageal cancer, uterine cancer, liver cancer, and cholangiocarcinoma or bile duct cancer. The present application provides such therapies.

SUMMARY OF THE INVENTION

The present invention relates to a method of treating cancers (e.g., esophageal adenocarcinoma) in a subject in need of treatment.

Accordingly, in one aspect, the present invention is a method of treating a cancer in a subject in need thereof. The cancer can be an esophageal cancer, a uterine cancer, a liver cancer, or a cholangiocarcinoma. Alternatively, the cancer can be a stomach cancer. The method comprises administering to the subject a therapeutically effective amount of an anti-Dkk-1 antibody or antigen binding-fragment thereof, wherein the subject is determined to have a constitutively activating mutation of the beta-catenin protein (SEQ ID NO:2).

In another aspect, the present invention is a method of treating a subject suffering from a cancer. The cancer can be an esophageal cancer, a uterine cancer, a liver cancer, or a cholangiocarcinoma. Alternatively, the cancer can be a stomach cancer. The method comprises the steps of obtaining a sample of a neoplastic cell from the subject; determining a sequence of the beta-catenin protein in the sample; and administering to the subject a therapeutically effective amount of an anti-Dkk-1 antibody or antigen binding-fragment thereof if the sequence of a beta-catenin protein (SEQ ID NO: 2) includes a constitutively activating mutation.

In yet another aspect, the present invention is a method of treating a cancer in a subject in need thereof. The cancer can be an esophageal cancer, a uterine cancer, a liver cancer, or a cholangiocarcinoma. Alternatively, the cancer can be a stomach cancer. The method comprises administering to the subject a therapeutically effective amount of an anti-Dkk-1 antibody or antigen binding-fragment thereof, wherein the subject has a constitutively activating mutation of the beta-catenin protein (SEQ ID NO: 2).

BRIEF DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

FIG. 1 is a table presenting the analysis of CTNNB1 (beta-catenin) protein mutational data in patients subject to DKN-01 therapy.

FIGS. 3A through 3F illustrate the sequence of the human CTNNB1 gene.

FIGS. 4A through 4D collectively represent Table 1 which shows examples of mutations of the beta-catenin protein.

DETAILED DESCRIPTION OF THE INVENTION

Figures 2A, 2B:
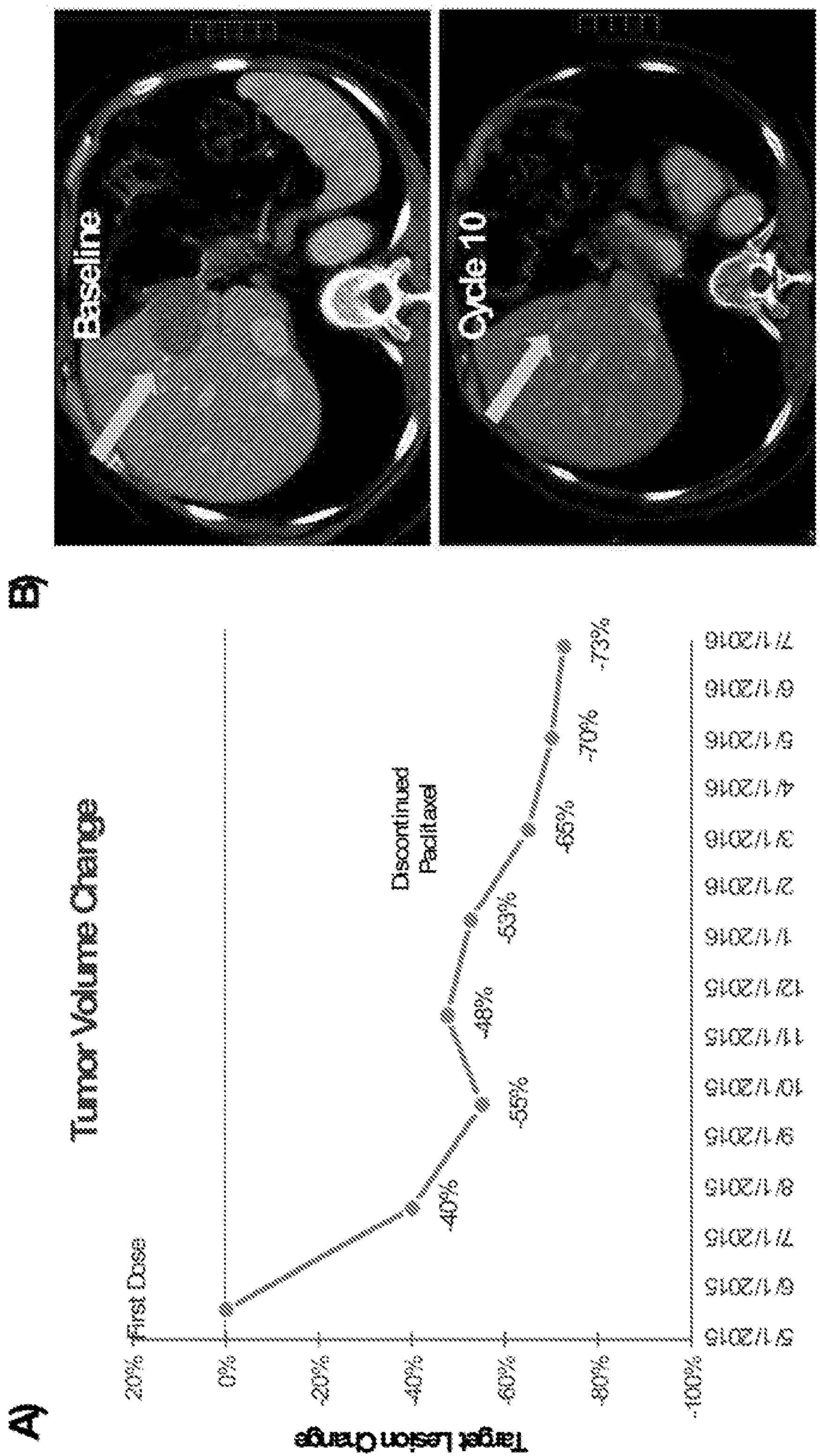
FIG. 2A is a plot indicating the change (in percent of size) in the lesion size in Patient 105-023 suffering from esophageal cancer and put on a combination therapy of Paclitaxel and DKN-01. Patient 105-023 was shown to have a deletion of exons 2 through 4 of the CTNNB1 (beta catenin) gene.
FIG. 2B is a tomographic image of the target lesion of Patient 105-023 at the inception of the study and at cycle 10.
Figure 4D:
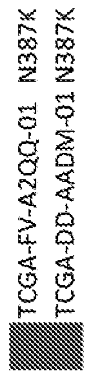

A description of example embodiments of the invention follows.

Dickkopf-1 (Dkk-1) is a protein that acts as a natural inhibitor of the canonical Wnt/β-catenin signaling pathway. The Wnt pathway influences a number of biological processes such as cell growth, cell proliferation, stem cell maintenance, cell differentiation, cell polarity, bone development, and adult tissue homeostasis.

In a canonical Wnt/β-catenin signaling pathway, extracellular Wnt ligand binds to its cognate receptor "Frizzled," and further recruits transmembrane lipoproteins LPR5 and LPR6 (low-density lipoprotein receptor-related proteins 5 and 6) co-receptors. Formation of a Wnt/Frizzled/LPR5/6 complex triggers several intracellular signaling cascades, including the one mediated by the β-catenin protein, a gene product of the CTNNB1 gene. In particular, the formation of a Wnt/Frizzled/LPR5/6 complex results in stabilization of cytoplasmic level of beta-catenin due to the inhibition of the beta-catenin phosphorylation. While phosphorylated beta-catenin is degraded in the cytoplasm, unphosphorylated beta-catenin translocates to the nucleus, where it enhances target gene expression of, e.g., cyclin D1, c-myc, c-jun, cyclooxygenase-2, matrix metalloproteinase-7, vascular endothelial growth factor, and survivin, among other growth factors. Absent the signal from the Wnt/Frizzled/LPR5/6 complex, beta-catenin is phosphorylated by intracellular kinases, such as glycogen synthase kinase 3β (GSK3β) and casein kinas I (CKI). Transduction of a signal from the Wnt/Frizzled/LPR5/6 complex inhibits this phosphorylation.

Extracellular Dkk-1 binds to the LPR5/6 co-receptors and prevents Wnt ligand binding. This results in resuming of beta-catenin phosphorylation and its subsequent degradation, thus inhibiting canonical Wnt signaling pathway.

See URL "https://www.ncbi.nlm.nih.gov/gene/1499" for the nucleotide sequence and genomic (chromosomal) coordinates of human CTNNB1. Briefly, genomic (chromosomal) coordinates of CTNNB1 gene are chr3:41,240,942-

41,281,939. All coordinates are from build GRCh37/hg19. Nucleotide sequence of CTNNB1 is provided in SEQ ID NO: 1 (includes exons, indicated by capital letters). The gene product of human CNNTB1 gene, referred herein as beta-catenin or beta-catenin protein, is a protein having the sequence provided by SEQ ID NO: 2 (UniProt accession No. P35222). Of particular interest are Exons 2, 3, and 4, corresponding in SEQ ID NO: 2 to amino acid residues 1 through 4 (Exon 2), 5-81 (Exon 3), and 82-165 (Exon 4). The amino acid sequences of the Exons 2 through 4 are provided by SEQ ID Nos: 3, 4, and 5, respectively.

As used herein, "a constitutively activating mutation of a beta-catenin protein" refers to a mutation of the amino acid sequence of beta-catenin that results in an elevated cellular level of beta-catenin functionally capable of transducing a signal to the cell nucleus, when compared to a wild type protein. Examples of constitutively activating mutations of beta-catenin include mutations that result in its inability to be phosphorylated by GSK3-beta kinase and/or casein kinase I in the absence of the Wnt/Frizzled/LPR5/6 complex. Examples of such mutations include: deletions of Exons 2 through 4, deletion of or within Exon 3, and mutations of the serine and threonine residues that are phosphorylated in the absence of the Wnt/Frizzled/LPR5/6 complex, such as Ser33, Ser37, Thr41, and Ser45 of SEQ ID NO: 2.

In various embodiments, a mutation of the beta-catenin protein is selected from the mutations listed in Table 1, represented in FIGS. 4A through 4D.

As those of skill in the art will recognize, "esophageal cancer" as used herein refers to cancer of the esophagus as well as the gastro-esophageal junction. As commonly used in the art, esophageal cancer comprises esophageal squamous cell carcinoma (ESCC) and esophageal adenocarcinoma (EAC). Generally, ESCC refers to cancer that originates in squamous cells, which cells line the esophagus in approximately upper ⅔ of the organ. EAC refers to cancer that originates in gland cells, which replace an area of squamous cells (e.g., in Barrett's esophagus), typically in the lower ⅓ of the esophagus. As such, esophageal adenocarcinoma as used herein refers to adenocarcinoma of the esophagus as well as the gastro-esophageal junction.

"Uterine cancer" is any type of cancer that emerges from the tissue of the uterus. It can refer to several types of cancer, with cervical cancer (arising from the lower portion of the uterus) being the most common type.

"Liver cancer," also known as hepatic cancer and primary hepatic cancer, is cancer that starts in the liver. Cancer which has spread from elsewhere to the liver, known as liver metastasis, is more common than that which starts in the liver. Primary liver cancer is globally the sixth most frequent cancer (6%) and the second leading cause of death from cancer (9%).

"Cholangiocarcinoma" or bile duct cancer is a form of cancer that is composed of mutated epithelial cells (or cells showing characteristics of epithelial differentiation) that originate in the bile ducts which drain bile from the liver into the small intestine. The rates of cholangiocarcinoma have been rising worldwide over the past few decades. Cholangiocarcinoma is considered to be an incurable and rapidly lethal cancer unless both the primary tumor and any metastases can be fully removed by surgery. No potentially curative treatment exists except surgery, but most people have advanced stage disease at presentation and are inoperable at the time of diagnosis.

"Stomach cancer" also called gastric cancer, is a cancer that starts in the stomach. About 90% to 95% of cancers of the stomach are adenocarcinomas. When the term stomach cancer or gastric cancer is used, it almost always refers to an adenocarcinoma. These cancers develop from the cells that form the innermost lining of the stomach (known as the mucosa).

The term "effective amount" means an amount of a therapeutic agent, e.g. an antibody, that is effective in prophylactically or therapeutically treating the indicated disorder. An "effective amount" may also refer to an amount of a combination of therapeutic agents that is therapeutically or prophylactically sufficient to treat the target disorder. An effective amount will depend on the age, gender, and weight of the patient, the current medical condition of the patient, and the nature of the esophageal cancer being treated. Those of skill in the art will be able to determine appropriate dosages depending on these and other factors.

It has now been discovered that cancer patients suffering from certain cancers and who have a constitutively activating mutation within the beta-catenin protein (SEQ ID NO: 2) are expected to be more responsive to an anti-Dkk-1 antibody therapy than patients who do not have such a mutation. Accordingly, the present invention relates to a method of treating cancers (e.g., esophageal cancer, uterine cancer, liver cancer, and cholangiocarcinoma) in a subject in need of treatment comprising administering an effective amount of an anti-Dkk-1 antibody, or antigen binding-fragment thereof, wherein the subject is determined to have a constitutively activating mutation of a beta-catenin protein (SEQ ID NO:2).

Dkk-1 Antibody

Dkk-1 antibodies have been described previously (see, e.g., U.S. Pat. Nos. 8,148,498 and 7,446,181, incorporated by reference herein in their entireties). The Dkk-1 antibody or antigen-binding fragment thereof disclosed herein relates to human engineered antibodies that bind to a human Dkk-1 comprising the amino acid sequence set for in SEQ ID NO: 27, or fragments thereof. The present Dkk-1 antibodies are therapeutically useful Dkk-1 antagonists possessing a number of desirable properties. For example, the Dkk-1 antibodies block Dkk-1 mediated inhibition of alkaline phosphatase, a marker or osteoblast activity, as well as treat various types of cancer (e.g., non-small cell lung cancer).

A full-length antibody as it exists naturally is an immunoglobulin molecule comprising 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with the well-known Kabat numbering convention.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

As used herein, the term "monoclonal antibody" (Mab) refers to an antibody that is derived from a single copy or clone including, for example, any eukaryotic, prokaryotic, or phage clone, and not the method by which it is produced. Mabs of the present invention preferably exist in a homogeneous or substantially homogeneous population. Complete Mabs contain 2 heavy chains and 2 light chains.

Unless specified otherwise, the term "Dkk-1 antibody" encompasses both a full-length antibody as well as an antigen binding-fragment of the Dkk-1 antibody.

"Antigen-binding fragments" of such monoclonal antibodies include, for example, Fab fragments, Fab' fragments, $F(ab')_2$ fragments, and single chain Fv fragments. Monoclonal antibodies and antigen-binding fragments thereof can be produced, for example, by recombinant technologies, phage display technologies, synthetic technologies, e.g., CDR-grafting, or combinations of such technologies, or other technologies known in the art. For example, mice can be immunized with human DKK-1 or fragments thereof, the resulting antibodies can be recovered and purified, and determination of whether they possess binding and functional properties similar to or the same as the antibody compounds disclosed herein can be assessed by the methods known in the art. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

Monoclonal Dkk-1 antibodies disclosed herein are engineered to comprise framework regions that are substantially human or fully human surrounding CDRs derived from a non-human antibody. "Antigen-binding fragments" of such human engineered antibodies include, for example, Fab fragments, Fab' fragments, $F(ab')_2$ fragments, and single chain Fv fragments. "Framework region" or "framework sequence" refers to any one of framework regions 1 to 4. Human engineered antibodies and antigen-binding fragments thereof encompassed by the antibodies disclosed herein include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, about 95%, or about 99% sequence identity to a known human germline framework sequence.

Human engineered antibodies in addition to those disclosed herein exhibiting similar functional properties can be generated using several different methods. The specific antibody compounds disclosed herein can be used as templates or parent antibody compounds to prepare additional antibody compounds. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816,397; 5,225,539, and 5,693,761; computer programs ABMOD and ENCAD as described in Levitt (1983) *J. Mol. Biol.* 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536). Methods for identifying residues to consider for back-mutation are known in the art (see, e.g., U.S. Pat. No. 8,148,498).

The methods provided herein relate to the use of a Dkk-1 antibody comprising a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2 and HCDR3, wherein LCDR1 has the amino sequence of SEQ ID NO: 6, HCDR1 has the amino sequence of SEQ ID NO: 9, and HCDR2 has the amino sequence of SEQ ID NO: 10.

In one embodiment, the Dkk-1 antibody comprises a LCDR1 having the amino sequence of SEQ ID NO: 6, LCDR2 having the amino sequence of SEQ ID NO: 7, LCDR3 having the amino sequence of SEQ ID NO: 8, HCDR1 having the amino sequence of SEQ ID NO: 9, HCDR2 having the amino sequence of SEQ ID NO: 10, and HCDR3 having the amino sequence of SEQ ID NO: 11.

In another embodiment, the Dkk-1 antibody comprises a LCVR having the amino acid sequence of SEQ ID NO: 12 and a HCVR having the amino acid sequence of SEQ ID NO: 13. In a particular embodiment, the LCVR comprises the amino acid sequence of SEQ ID NO: 16 and the HCVR comprises the amino acid sequence of SEQ ID NO: 17.

In further embodiments, the Dkk-1 antibody comprises a heavy chain (HC) having the amino acid sequence of SEQ ID NO: 22 and a light chain (LC) having the amino acid sequence of SEQ ID NO: 23. The Dkk-1 antibody or antigen binding-fragment thereof comprising the HC and LC amino acid sequence of SEQ ID NO: 22 and SEQ ID NO: 23, respectively, is referred to herein as DKN-01. In particular, DKN-01 has the molecular/empirical formula $C_{6394}H_{9810}N_{1698}O_{2012}S_{42}$ and a molecular weight of 144015 Daltons (intact).

In certain embodiments, the Dkk-1 antibody disclosed herein is an $IgG_4$ antibody with a neutralizing activity against human Dkk-1 comprising the sequence set forth in SEQ ID NO: 27, of a fragment thereof. For example, canonical Wnt signaling is important for osteoblast differentiation and activity. Wnt-3a combined with BMP-4 induces pluripotent mouse C2C12 cells to differentiate into osteoblasts with a measurable endpoint of alkaline phosphatase ("AP"), a marker of osteoblast activity. Dkk-1, an inhibitor of canonical Wnt signaling, inhibits the differentiation and production of AP. Neutralizing Dkk-1 antibodies prevent Dkk-1-mediated inhibition of AP. Antibodies which block Dkk-1 inhibitory activity prevent the loss of AP activity (see U.S. Pat. No. 8,148,498). In a particular embodiment, the Dkk-1 antibody possessing neutralizing activity is DKN-01, which is an $IgG_4$ antibody.

The Dkk-1 antibodies disclosed herein possess high affinity (Kd) to Dkk-1 (e.g., human Dkk-1, SEQ ID NO: 27), as described in U.S. Pat. No. 8,148,498. For example, the present Dkk-1 antibodies possess a Kd of between $0.5\times10^{-12}$ M and $3.0\times10^{-11}$ M, at 37° C.

Modes of Administration

The Dkk-1 antibody and chemotherapeutic agents for use in the methods or compositions of the invention can be formulated for parenteral, oral, transdermal, sublingual, buccal, rectal, intranasal, intrabronchial or intrapulmonary administration.

For parenteral administration, the compounds for use in the methods or compositions of the invention can be formulated for injection or infusion, for example, intravenous, intramuscular or subcutaneous injection or infusion, or for administration in a bolus dose and/or infusion (e.g., continuous infusion). Suspensions, solutions or emulsions in an oily or aqueous vehicle, optionally containing other formulatory agents such as suspending, stabilizing and/or dispersing agents can be used.

For oral administration the compounds can be of the form of tablets or capsules prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycolate); or wetting agents (e.g., sodium lauryl sulphate). If desired, the tablets can be coated using suitable methods. Liquid preparation for oral administration can be in the form of solutions, syrups or suspensions. The liquid preparations can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

For buccal administration, the compounds for use in the methods or compositions of the invention can be in the form of tablets or lozenges formulated in a conventional manner.

For rectal administration, the compounds for use in the methods or compositions of the invention can be in the form of suppositories.

For sublingual administration, tablets can be formulated in conventional manner.

For intranasal, intrabronchial or intrapulmonary administration, conventional formulations can be employed.

Further, the compounds for use in the methods or compositions of the invention can be formulated in a sustained release preparation. For example, the compounds can be formulated with a suitable polymer or hydrophobic material which provides sustained and/or controlled release properties to the active agent compound. As such, the compounds for use in the method of the invention can be administered in the form of microparticles, for example, by injection or in the form of wafers or discs by implantation. Various methods of formulating controlled release drug preparations are known in the art.

Administration of a compound, or pharmaceutically acceptable salt thereof, or a composition comprising one or more compound (or pharmaceutical salt thereof) of the invention useful to practice the methods described herein, can be continuous, hourly, four times daily, three time daily, twice daily, once daily, once every other day, twice weekly, once weekly, once every two weeks, once a month, or once every two months, or longer, or some other intermittent dosing regimen.

Examples of administration of a compound, or a composition comprising one or more compound (or pharmaceutical salt thereof) of the invention include peripheral administration. Examples of peripheral administration include oral, subcutaneous, intraperitoneal, intramuscular, intravenous, rectal, transdermal, or intranasal forms of administration.

As used herein, peripheral administration includes all forms of administration of a compound or a composition comprising a compound of the instant invention which excludes intracranial administration. Examples of peripheral administration include, but are not limited to, oral, parenteral (e.g., intramuscular, intraperitoneal, intravenous or subcutaneous injection, extended release, slow release implant, depot and the like), nasal, vaginal, rectal, sublingual or topical routes of administration, including transdermal patch applications and the like.

Combination Therapy

The Dkk-1 antibody disclosed herein can be used for treating esophageal cancer in combination with a second amount of a chemotherapeutic agent (sometime referred to herein as a "second agent"). Such combination administration can be by means of a single dosage form which includes a Dkk-1 antibody and the second agent, such single dosage form including a tablet, capsule, spray, inhalation powder, injectable liquid or the like. Combination administration can comprise a further second agent (e.g., chemotherapeutic agent) in addition to the single dosage form. Alternatively, combination administration can be by means of administration of two different dosage forms, with one dosage form containing a Dkk-1 antibody, and the other dosage form including a second amount of a chemotherapeutic agent. In this instance, the dosage forms may be the same or different. Without wishing to limit combination therapies, the following exemplifies certain combination therapies which may be employed. It is understood that additional chemotherapeutic agents beyond the required second amount of a chemotherapeutic agent can be employed in the method described herein.

The second amount of the chemotherapeutic agent (sometimes referred to herein as the second agent) can be administered before, simultaneously with, or after the administration of a Dkk-1 antibody. Accordingly, a Dkk-1 antibody and a second agent can be administered together in a single formulation or can be administered in separate formulations, e.g., either simultaneously or sequentially, or both. For example, if a Dkk-1 antibody and a second agent are administered sequentially in separate compositions, the Dkk-1 antibody can be administered before or after the chemotherapeutic agent. The duration of time between the administration of a Dkk-1 antibody and the second amount of the chemotherapeutic agent will depend on the nature of the chemotherapeutic agent. In certain embodiments, the Dkk-1 antibody can precede or follow a chemotherapeutic agent immediately, or after some duration of time deemed to be appropriate by a skilled practitioner.

In addition, the Dkk-1 antibody and the second amount of the chemotherapeutic agent may or may not be administered on similar dosing schedules. For example, the Dkk-1 antibody and the chemotherapeutic agent may have different half-lives and/or act on different time-scales such that the Dkk-1 antibody is administered with greater frequency than the chemotherapeutic agent or vice-versa. For example, the Dkk-1 antibody and the chemotherapeutic agent can be administered together (e.g., in a single dosage or sequentially) on one day, followed by administration of only the chemotherapeutic agent (or a different chemotherapeutic) a set number of days later. The number of days in between administration of therapeutic agents can be appropriately determined according to the safety and pharmacodynamics of each drug. Either the Dkk-1 antibody or the chemotherapeutic agent can be administered acutely or chronically.

As used herein, an "effective amount" refers to an amount of a therapeutic agent or a combination of therapeutic agents that is therapeutically or prophylactically sufficient to treat the target disorder. An effective amount will depend on the age, gender, and weight of the patient, the current medical condition of the patient, and the nature of the esophageal cancer being treated. Those of skill in the art will be able to determine appropriate dosages depending on these and other factors.

Suitable doses per administration for a Dkk-1 antibody include doses of about or greater than about 15 mg, about 20 mg, about 30 mg, about 40 mg, about 50 mg, about 100 mg, about 200 mg, about 300 mg, about 400 mg, about 500 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, or about 3,000 mg. Each suitable dose can be administered over a period time deemed appropriate by a skilled practitioner. For example, each suitable dose can be administered over a period of about 30 minutes and up to about 1 hour, about 2 hours, about 3, hours, about 4 hours, about 5 hours, about 6 hours, about 7 hours, or about 8 hours. In a particular embodiment, a suitable dose for Dkk-1 antibody can be about 150 mg administered over a period of about 30 minutes and up to about 2 hours. Another suitable dose for the Dkk-1 antibody can be about 300 mg administered over a period of about 30 minutes and up to about 2 hours.

Suitable doses per administration for a second amount of chemotherapeutic agent can be determined based on the recommended dosing found on the label. When paclitaxel in the second amount of the chemotherapeutic agent used doses of about or greater than about 8 mg/m$^2$, 10 mg/m$^2$, about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, about 100 mg/m$^2$, about 105 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 225 mg/m$^2$, about 250 mg/m$^2$, about 275 mg/m$^2$, about 300 mg/m$^2$, about 600 mg/m$^2$ or about 800 mg/m$^2$. For example, a suitable dose per administration of paclitaxel is about 80 mg/m$^2$ over a period of about 1 hour.

An effective amount can be achieved in the methods or compositions of the invention by coadministering a first amount of a Dkk-1 antibody (or a pharmaceutically acceptable salt, hydrate or solvate thereof) and a second amount of at least one chemotherapeutic agent. In one embodiment, the Dkk-1 antibody and the chemotherapeutic agent are each administered in a respective effective amount (e.g., each in an amount which would be therapeutically effective if administered alone). In another embodiment, the Dkk-1 antibody and the chemotherapeutic agent are each administered in an amount which alone does not provide a therapeutic effect (a sub-therapeutic dose). In yet another embodiment, the Dkk-1 antibody can be administered in an effective amount, while the chemotherapeutic agent is administered in a sub-therapeutic dose. In still another embodiment, the Dkk-1 antibody can be administered in a sub-therapeutic dose, while the chemotherapeutic agent is administered in an effective amount.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein "treating" includes achieving, partially or substantially, delaying, inhibiting or preventing the progression of clinical indications related to the cancer being treated. For example, "treating" includes reduction in tumor growth, or prevention of further growth, as detected by standard imaging methods known in the art, including, for example, computed tomography (CT) scan, magnetic resonance imaging (MRI), chest x-ray, and CT/positron emission tomography (CT/PET) scans, and evaluated according to guidelines and methods known in the art. For example, responses to treatment can be evaluated through the Response Evaluation Criteria in Solid Tumors (RECIST) (Revised RECIST Guideline version 1.1; see Eisenhauer et al., *Eur. J. Cancer* 45(2):228-47, 2009). Thus, in some embodiments, "treating" refers to a Complete Response (CR), which is defined according to the RECIST guideline as the disappearance of all target lesions, or a Partial Response (PR), which is defined as at least a 30% decrease in the sum of diameter of target lesions, taking as reference the baseline sum diameters. Other means for evaluating tumor response to treatment include evaluation of tumor markers and evaluation of performance status (e.g., assessment of creatinine clearance; see Cockcroft and Gault, *Nephron.* 16:31-41, 1976).

Pharmaceutical Composition

The Dkk-1 antibody and chemotherapeutic agents disclosed herein can be incorporated into pharmaceutical compositions suitable for administration. Such compositions typically comprise the antibody, or one or more chemotherapeutic agents, or both, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Dkk-1antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid-derivatives. Transmucosal administration can be accomplished through the use of nasal sprays or suppositories.

For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

While this invention has been particularly shown and described with references to example embodiments thereof, it will be understood by those skilled in the art that various changes in form and details may be made therein without departing from the scope of the invention encompassed by the appended claims.

EXEMPLIFICATION

Example 1—Detection of Constitutively Activating Mutations of CTNNB1 Gene

Biopsy samples can be obtained from a patient for determination of the sequence of the beta-catenin gene. Gene sequencing is well within the purview of a person of ordinary skill in the art, and can be accomplished using commercially available products, such as the Archer® VariantPlex Solid Tumor kit available from ArcherDX, Inc. of Boulder, Colo., and next generation sequencing platforms such as one available from Illumina, Inc. of San Diego, Calif. (Worldwide Headquarters). Comparison can be done to publically available genetic sequence of the gene, e.g. at the NCBI database.

Example 2—Detection of Constitutively Activating Mutations of Beta-Catenin Protein Phosphorylation status of beta-catenin can be determined by western blot analysis with antibodies that recognize the phosphorylated form of beta-catenin. Stabilization and activation of beta-catenin can be determined by western blot demonstrating an increase in cellular protein levels and by immunofluorescence demonstrating nuclear localization of beta-catenin. Measuring the expression of downstream beta-catenin target genes or an exogenous beta-catenin reporter gene construct can be utilized to determine the activation status of beta-catenin.

Example 3—CTNNB1 Mutational Data in Patients Subject to DKN-01 Therapy

Clinical Study of the Paclitaxel/DKN-01 Combination Therapy

Patients were selected for a clinical investigation of the combination DKN-01/Paclitaxel® therapy designed as a phase 1 non-randomized, dose-escalating, open label, multicenter study.

Patients with histologically confirmed recurrent or metastatic esophageal or gastro-esophageal junction adenocarcinoma were selected. Each patient reported on in Table 1 was placed on a 28-day treatment cycle: 300 mg of DKN-01 antibody on days 1 and 15; 80 mg/m$^2$ of Paclitaxel® on days 1, 8, 15, and 22.

DKN-01 was administered intravenously (IV) over a minimum of 30 minutes and up to a maximum of 2 hours without interruption. Paclitaxel® was administered IV over 1 hour on days 1, 8, 15 and 22 of each cycle according to standard clinical practice. Standard of care premedication for paclitaxel was given prior to administration. Sequence of administration: pre-medication for paclitaxel, DKN-01, pactlitaxel. DKN-01 was administered first followed by paclitaxel on Days 1 and 15 when both drugs were delivered.

Biopsy samples, collected prior to commencement of the study, were subject to gene expression analysis.

Radiological tumor assessment was performed. At a minimum, a computerized tomography (CT) scan of the chest, abdomen and pelvis had been conducted for tumor assessment with documentation of one or more metastatic tumors measurable on radiographic imaging as defined by Response Evaluation Criteria in Solid Tumors (RECIST). Whenever feasible, the preferred imaging modality throughout the study was CT/PET scans. Baseline radiographic tumor assessments were conducted within 28 days prior to day 1 of cycle 1 and subsequent tumor assessments were performed after every even numbered cycle.

The following response criteria were used:

Complete Response (CR): Disappearance of all lesions. Any pathological lymph nodes had reduction in short axis to <10 mm. Tumor marker results were normalized.

Partial Response (PR): At least a 30% decrease in the sum of diameter of lesions, taking as reference the baseline sum diameters.

Progressive Disease (PD): At least a 20% increase in the sum of the diameters of lesions, taking as reference the smallest sum on study (including the baseline sum if that is the smallest). In addition to the relative increase of 20%, the sum demonstrated an absolute increase of at least 5 mm. The appearance of one or more new lesions was also considered progression.

Stable Disease (SD): Neither sufficient shrinkage to qualify for PR nor sufficient increase to qualify for PD, taking as reference the smallest sum diameters while on study.

Result Analysis

Analysis of beta-catenin mutations was performed on patients subjected to the combination therapy of Paclitaxel® and DKN-01 according to the methods described above. The results are presented in FIG. 1. As can be seen, the beta-catenin mutations resulting from deletion of Exons 2-4, S45F and T41I are found in patients exhibiting a partial response or at least stable disease.

This data demonstrates that an activating mutation of beta-catenin is a biomarker predictor of a therapeutic response to an anti-Dkk-1 antibody administration.

Example 4—Case Study of Patient 105-023: β-Catenin Activating Mutations is a Biomarker for DKN-01 Sensitivity in Esophageal Cancer Therapy As shown in FIG. 1, Patient 105-023, suffering from a GEJ adenocarcinoma malignancy, exhibited the highest reduction in tumor volume. Clinical data pertaining to Patient 105-023 was further analyzed.

Patient 105-023 experienced a tumor regression of 73% over the course of fourteen 28-day treatment cycles. The results are illustrated in FIG. 2A and FIG. 2B. FIG. 2A shows a plot of tumor volume in Patient 105-023 as a function of the number of cycles of treatment (cycles are denoted by start dates). Patient 105-023 received 300 mg of DKN-01 on Days 1 and 15 and 80 mg/m2 of paclitaxel weekly during a 28-Day Cycle for the first 10 cycles. During Cycle 10 paclitaxel was discontinued; however the response continued to deepen. FIG. 2B is a computerized tomography image demonstrating a reduction in the size of the primary lesion in Patient 105-023 from baseline to Cycle 10. Arrow denotes the primary lesion.

As can be seen from the data, Patient 105-023 discontinued paclitaxel in Cycle 10 and has continued to have a deepening response to DKN-01 monotherapy. Genetic analysis of a biopsy sample from this patient's tumor (performed using the methods described in Example 1 by employing a FoundationOne® Panel, commercially available from Foundation Medicine, Inc., Cambridge, Mass.) indicated the presence of a β-catenin exon 2-4 deletion that results in constitutive activation.

This data further supports the finding that an activating mutation of beta-catenin is a biomarker predictor of a therapeutic response to an anti-Dkk-1 antibody administration.

SEQUENCES

The Genomic DNA Sequence of CTNNB1—SEQ ID NO: 1

SEQ ID NO: 1, shown in FIGS. 3A through 3F, represents the sequence of human CTNNB1 gene having the chromosomal coordinates chr3:41,240,942-41,281,939. All coordinates are from build GRCh37/hg19. 5'UTR and 3'UTR exons are not included. Capital letters are the exons, lower case letters are introns. Exons 2, 3, and 4 are underlined and superscripted.

Amino Acid Sequence of beta-Catenin Protein—SEQ ID NO: 2

SEQ ID NO: 2, below, is the amino acid sequence of human beta-catenin, a 781 amino acid protein UniProt Database ID—P35222 (http://www.uniprot.org/uniprot/P35222). Exons 2, 3, and 4 are underlined and superscripted.

```
2   4 3   10         20         30         40
MATQ ADLMEL DMAMEPDRKA AVSHWQQQSY LDSGIHSGAT

        50         60         70         80
TTAPSLSGKG NPEEEDVDTS QVLYEWEQGF SQSFTQEQVA

4       90        100        110        120
DIDGQYAMTR AQRVRAAMFP ETLDEGMQIP STQFDAAHPT

       130        140        150        160
NVQRLAEPSQ MLKHAVVNLI NYQDDAELAT RAIPELTKLL

       170        180        190        200
NDEDQVVVNK AAVMVHQLSK KEASRHAIMR SPQMVSAIVR

       210        220        230        240
TMQNTNDVET ARCTAGTLHN LSHHREGLLA IFKSGGIPAL

       250        260        270        280
VKMLGSPVDS VLFYAITTLH NLLLHQEGAK MAVRLAGGLQ

       290        300        310        320
KMVALLNKTN VKFLAITTDC LQILAYGNQE SKLIILASGG

       330        340        350        360
```

-continued

```
PQALVNIMRT YTYEKLLWTT SRVLKVLSVC SSNKPAIVEA

       370        380        390        400
GGMQALGLHL TDPSQRLVQN CLWTLRNLSD AATKQEGMEG

       410        420        430        440
LLGTLVQLLG SDDINVVTCA AGILSNLTCN NYKNKMMVCQ

       450        460        470        480
VGGIEALVRT VLRAGDREDI TEPAICALRH LTSRHQEAEM

       490        500        510        520
AQNAVRLHYG LPVVVKLLHP PSHWPLIKAT VGLIRNLALC

       530        540        550        560
PANHAPLREQ GAIPRLVQLL VRAHQDTQRR TSMGGTQQQF

       570        580        590        600
VEGVRMEEIV EGCTGALHIL ARDVHNRIVI RGLNTIPLFV

       610        620        630        640
QLLYSPIENI QRVAAGVLCE LAQDKEAAEA IEAEGATAPL

       650        660        670        680
TELLHSRNEG VATYAAAVLF RMSEDKPQDY KKRLSVELTS

       690        700        710        720
SLFRTEPMAW NETADLGLDI GAQGEPLGYR QDDPSYRSFH

       730        740        750        760
SGGYGQDALG MDPMMEHEMG GHHPGADYPV DGLPDLGHAQ

       770        780
DLMDGLPPGD SNQLAWFDTD L
```

Exons of Beta-Catenin Protein

The amino acid number range does not correspond exactly to the exons as marked in SEQ ID NO: 1 because of the splicing of the transcript. For example the first base "G" of the codon for amino acid #5 is in exon 2 and second and third bases "CT" are in Exon 3.

Highlighted residues of Exon 3 (in bold and underlined) indicate GSK3B and CK1α phosphorylation sites that stabilize beta-catenin when they are mutated or deleted): S33, S37, T41, S45. (See de La Coste A, Romagnolo B, Billuart P, Renard C A, Buendia M A, Soubrane O, et al. (1998). Somatic mutations of the beta-catenin gene are frequent in mouse and human hepatocellular carcinomas. Proc Natl Acad Sci USA 95: 8847-8851; and Xu W, & Kimelman D (2007). Mechanistic insights from structural studies of beta-catenin and its binding partners. J Cell Sci 120: 3337-3344.)

Exon 1
(Non-Coding)

Exon 2-SEQ ID NO: 3 (amino acids 1-4 of SEQ ID NO: 2)

(SEQ ID NO: 3)

MATQ

Exon 3-SEQ ID NO: 4 (amino acids 5-81 of SEQ ID NO: 2)

(SEQ ID NO: 4)

ADLMELDMAMEPDRKAAVSHWQQQSYLDSGIHSGATTTAPSLSGKGNPEEEDVDTSQVLYEWEQGFSQSFTQEQVAD

Exon 4-SEQ ID NO: 5 (amino acids 82-165 of SEQ ID NO: 2)

(SEQ ID NO: 5)

IDGQYAMTRAQRVRAAMFPETLDEGMQIPSTQFDAAHPTNVQRLAEPSQMLKHAVVNLINYQDDAELATRAIPELTKLLNDEDQ

LCDR1

(SEQ ID NO: 6)

His Ala Ser Asp Ser Ile Ser Asn Ser Leu His

LCDR2

(SEQ ID NO: 7)

Tyr Xaa Arg Gln Ser Xaa Gln
wherein Xaa at position 2 is Gly or Ala; and Xaa at position 6 is Ile or Glu -continued

LCDR3

(SEQ ID NO: 8)

Gln Gln Ser Xaa Ser Trp Pro Leu His
wherein Xaa at position 4 is Glu or Ala

HCDR1

(SEQ ID NO: 9)

Gly Phe Thr Phe Ser Ser Tyr Thr Met Ser

HCDR2

(SEQ ID NO: 10)

Thr Ile Ser Gly Gly Gly Phe Gly Thr Tyr Tyr Pro Asp Ser Val Lys

HCDR3

(SEQ ID NO: 11)

Pro Gly Tyr Xaa Asn Tyr Tyr Phe Asp Ile
wherein Xaa at position 4 is His or Asn

LCVR (SEQ ID NO: 12)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Xaa Arg Gln Ser Xaa Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Xaa Ser Trp Pro Leu His Phe Gly Gly Gly Thr Lys Val Glu Ile Lys
wherein Xaa at position 51 is Gly or Ala; Xaa at position 55 is Ile or Glu and Xaa at position 92 is Glu or Ala.

HCVR (SEQ ID NO: 13)

Glu Val Gln Leu Val Glu Ser Gly Gly Gly Leu Val Gln Pro Gly Gly Ser Leu Arg Leu Ser

Cys Ala Ala Ser Gly Phe Thr Phe Ser Ser Tyr Thr Met Ser Trp Val Arg Gln Ala Pro Gly Lys

Gly Leu Glu Trp Val Ala Thr Ile Ser Gly Gly Gly Phe Gly Thr Tyr Tyr Pro Asp Ser Val Lys

Gly Arg Phe Thr Ile Ser Arg Asp Asn Ala Lys Asn Ser Leu Tyr Leu Gln Met Asn Ser Leu

Arg Ala Glu Asp Thr Ala Val Tyr Tyr Cys Ala Arg Pro Gly Tyr Xaa Asn Tyr Tyr Phe Asp

Ile Trp Gly Gln Gly Thr Thr Val Thr Val Ser Ser
wherein Xaa at position 102 is His or Asn

LCVR (SEQ ID NO: 14)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Gly Arg Gln Ser Ile Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Glu Ser Trp Pro Leu His Phe Gly Gly Gly Thr Lys Val Glu Ile Lys

HCVR (SEQ ID NO: 15)

Glu Val Gln Leu Val Glu Ser Gly Gly Gly Leu Val Gln Pro Gly Gly Ser Leu Arg Leu Ser

Cys Ala Ala Ser Gly Phe Thr Phe Ser Ser Tyr Thr Met Ser Trp Val Arg Gln Ala Pro Gly Lys

Gly Leu Glu Trp Val Ala Thr Ile Ser Gly Gly Gly Phe Gly Thr Tyr Tyr Pro Asp Ser Val Lys

Gly Arg Phe Thr Ile Ser Arg Asp Asn Ala Lys Asn Ser Leu Tyr Leu Gln Met Asn Ser Leu

Arg Ala Glu Asp Thr Ala Val Tyr Tyr Cys Ala Arg Pro Gly Tyr His Asn Tyr Tyr Phe Asp Ile

Trp Gly Gln Gly Thr Thr Val Thr Val Ser Ser

LCVR (SEQ ID NO: 16)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Ala Arg Gln Ser Ile Gln Gly Ile Pro Ala Arg Phe Ser Gly Ser Gly

-continued

Ser Gly Thr Asp Phe Thr Leu Thr Ile Ser Ser Leu Glu Pro Glu Asp Phe Ala Val Tyr Tyr Cys

Gln Gln Ser Glu Ser Trp Pro Leu His Phe Gly Gly Gly Thr Lys Val Glu Ile Lys

HCVR (SEQ ID NO: 17)

Glu Val Gln Leu Val Glu Ser Gly Gly Gly Leu Val Gln Pro Gly Gly Ser Leu Arg Leu Ser

Cys Ala Ala Ser Gly Phe Thr Phe Ser Ser Tyr Thr Met Ser Trp Val Arg Gln Ala Pro Gly Lys

Gly Leu Glu Trp Val Ala Thr Ile Ser Gly Gly Gly Phe Gly Thr Tyr Tyr Pro Asp Ser Val Lys

Gly Arg Phe Thr Ile Ser Arg Asp Asn Ala Lys Asn Ser Leu Tyr Leu Gln Met Asn Ser Leu

Arg Ala Glu Asp Thr Ala Val Tyr Tyr Cys Ala Arg Pro Gly Tyr Asn Asn Tyr Tyr Phe Asp

Ile Trp Gly Gln Gly Thr Thr Val Thr Val Ser Ser

LCVR (SEQ ID NO: 18)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Gly Arg Gln Ser Ile Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Ala Ser Trp Pro Leu His Phe Gly Gly Gly Thr Lys Val Glu Ile Lys

LCVR (SEQ ID NO: 19)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Ala Arg Gln Ser Glu Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Ala Ser Trp Pro Leu His Phe Gly Gly Gly Thr Lys Val Glu Ile Lys

HC (SEQ ID NO: 20)

Glu Val Gln Leu Val Glu Ser Gly Gly Gly Leu Val Gln Pro Gly Gly Ser Leu Arg Leu Ser

Cys Ala Ala Ser Gly Phe Thr Phe Ser Ser Tyr Thr Met Ser Trp Val Arg Gln Ala Pro Gly Lys

Gly Leu Glu Trp Val Ala Thr Ile Ser Gly Gly Gly Phe Gly Thr Tyr Tyr Pro Asp Ser Val Lys

Gly Arg Phe Thr Ile Ser Arg Asp Asn Ala Lys Asn Ser Leu Tyr Leu Gln Met Asn Ser Leu

Arg Ala Glu Asp Thr Ala Val Tyr Tyr Cys Ala Arg Pro Gly Tyr His Asn Tyr Tyr Phe Asp Ile

Trp Gly Gln Gly Thr Thr Val Thr Val Ser Ser Ala Ser Thr Lys Gly Pro Ser Val Phe Pro Leu

Ala Pro Cys Ser Arg Ser Thr Ser Glu Ser Thr Ala Ala Leu Gly Cys Leu Val Lys Asp Tyr Phe

Pro Glu Pro Val Thr Val Ser Trp Asn Ser Gly Ala Leu Thr Ser Gly Val His Thr Phe Pro Ala

Val Leu Gln Ser Ser Gly Leu Tyr Ser Leu Ser Ser Val Val Thr Val Pro Ser Ser Ser Leu Gly

Thr Lys Thr Tyr Thr Cys Asn Val Asp His Lys Pro Ser Asn Thr Lys Val Asp Lys Arg Val

Glu Ser Lys Tyr Gly Pro Pro Cys Pro Pro Cys Pro Ala Pro Glu Ala Ala Gly Gly Pro Ser Val

Phe Leu Phe Pro Pro Lys Pro Lys Asp Thr Leu Met Ile Ser Arg Thr Pro Glu Val Thr Cys Val

Val Val Asp Val Ser Gln Glu Asp Pro Glu Val Gln Phe Asn Trp Tyr Val Asp Gly Val Glu

Val His Asn Ala Lys Thr Lys Pro Arg Glu Glu Gln Phe Asn Ser Thr Tyr Arg Val Val Ser Val

Leu Thr Val Leu His Gln Asp Trp Leu Asn Gly Lys Glu Tyr Lys Cys Lys Val Ser Asn Lys

Gly Leu Pro Ser Ser Ile Glu Lys Thr Ile Ser Lys Ala Lys Gly Gln Pro Arg Glu Pro Gln Val

Tyr Thr Leu Pro Pro Ser Gln Glu Glu Met Thr Lys Asn Gln Val Ser Leu Thr Cys Leu Val

Lys Gly Phe Tyr Pro Ser Asp Ile Ala Val Glu Trp Glu Ser Asn Gly Gln Pro Glu Asn Asn Tyr

-continued

Lys Thr Thr Pro Pro Val Leu Asp Ser Asp Gly Ser Phe Phe Leu Tyr Ser Arg Leu Thr Val

Asp Lys Ser Arg Trp Gln Glu Gly Asn Val Phe Ser Cys Ser Val Met His Glu Ala Leu His

Asn His Tyr Thr Gln Lys Ser Leu Ser Leu Ser Leu Gly

LC (SEQ ID NO: 21)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Gly Arg Gln Ser Ile Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Glu Ser Trp Pro Leu His Phe Gly Gly Gly Thr Lys Val Glu Ile Lys Arg Thr Val

Ala Ala Pro Ser Val Phe Ile Phe Pro Pro Ser Asp Glu Gln Leu Lys Ser Gly Thr Ala Ser Val

Val Cys Leu Leu Asn Asn Phe Tyr Pro Arg Glu Ala Lys Val Gln Trp Lys Val Asp Asn Ala

Leu Gln Ser Gly Asn Ser Gln Glu Ser Val Thr Glu Gln Asp Ser Lys Asp Ser Thr Tyr Ser Leu

Ser Ser Thr Leu Thr Leu Ser Lys Ala Asp Tyr Glu Lys His Lys Val Tyr Ala Cys Glu Val Thr

His Gln Gly Leu Ser Ser Pro Val Thr Lys Ser Phe Asn Arg Gly Glu Cys

HC (SEQ ID NO: 22)

Glu Val Gln Leu Val Glu Ser Gly Gly Gly Leu Val Gln Pro Gly Gly Ser Leu Arg Leu Ser

Cys Ala Ala Ser Gly Phe Thr Phe Ser Ser Tyr Thr Met Ser Trp Val Arg Gln Ala Pro Gly Lys

Gly Leu Glu Trp Val Ala Thr Ile Ser Gly Gly Gly Phe Gly Thr Tyr Tyr Pro Asp Ser Val Lys

Gly Arg Phe Thr Ile Ser Arg Asp Asn Ala Lys Asn Ser Leu Tyr Leu Gln Met Asn Ser Leu

Arg Ala Glu Asp Thr Ala Val Tyr Tyr Cys Ala Arg Pro Gly Tyr Asn Asn Tyr Tyr Phe Asp

Ile Trp Gly Gln Gly Thr Thr Val Thr Val Ser Ser Ala Ser Thr Lys Gly Pro Ser Val Phe Pro

Leu Ala Pro Cys Ser Arg Ser Thr Ser Glu Ser Thr Ala Ala Leu Gly Cys Leu Val Lys Asp Tyr

Phe Pro Glu Pro Val Thr Val Ser Trp Asn Ser Gly Ala Leu Thr Ser Gly Val His Thr Phe Pro

Ala Val Leu Gln Ser Ser Gly Leu Tyr Ser Leu Ser Ser Val Val Thr Val Pro Ser Ser Ser Leu

Gly Thr Lys Thr Tyr Thr Cys Asn Val Asp His Lys Pro Ser Asn Thr Lys Val Asp Lys Arg

Val Glu Ser Lys Tyr Gly Pro Pro Cys Pro Pro Cys Pro Ala Pro Glu Ala Ala Gly Gly Pro Ser

Val Phe Leu Phe Pro Pro Lys Pro Lys Asp Thr Leu Met Ile Ser Arg Thr Pro Glu Val Thr Cys

Val Val Val Asp Val Ser Gln Glu Asp Pro Glu Val Gln Phe Asn Trp Tyr Val Asp Gly Val

Glu Val His Asn Ala Lys Thr Lys Pro Arg Glu Glu Gln Phe Asn Ser Thr Tyr Arg Val Val

Ser Val Leu Thr Val Leu His Gln Asp Trp Leu Asn Gly Lys Glu Tyr Lys Cys Lys Val Ser

Asn Lys Gly Leu Pro Ser Ser Ile Glu Lys Thr Ile Ser Lys Ala Lys Gly Gln Pro Arg Glu Pro

Gln Val Tyr Thr Leu Pro Pro Ser Gln Glu Glu Met Thr Lys Asn Gln Val Ser Leu Thr Cys

Leu Val Lys Gly Phe Tyr Pro Ser Asp Ile Ala Val Glu Trp Glu Ser Asn Gly Gln Pro Glu Asn

Asn Tyr Lys Thr Thr Pro Pro Val Leu Asp Ser Asp Gly Ser Phe Phe Leu Tyr Ser Arg Leu

Thr Val Asp Lys Ser Arg Trp Gln Glu Gly Asn Val Phe Ser Cys Ser Val Met His Glu Ala

Leu His Asn His Tyr Thr Gln Lys Ser Leu Ser Leu Ser Leu Gly

LC (SEQ ID NO: 23)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Ala Arg Gln Ser Ile Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

-continued

Gln Gln Ser Glu Ser Trp Pro Leu His Phe Gly Gly Gly Thr Lys Val Glu Ile Lys Arg Thr Val

Ala Ala Pro Ser Val Phe Ile Phe Pro Pro Ser Asp Glu Gln Leu Lys Ser Gly Thr Ala Ser Val

Val Cys Leu Leu Asn Asn Phe Tyr Pro Arg Glu Ala Lys Val Gln Trp Lys Val Asp Asn Ala

Leu Gln Ser Gly Asn Ser Gln Glu Ser Val Thr Glu Gln Asp Ser Lys Asp Ser Thr Tyr Ser Leu

Ser Ser Thr Leu Thr Leu Ser Lys Ala Asp Tyr Glu Lys His Lys Val Tyr Ala Cys Glu Val Thr

His Gln Gly Leu Ser Ser Pro Val Thr Lys Ser Phe Asn Arg Gly Glu Cys

HC (SEQ ID NO: 24)

Glu Val Gln Leu Val Glu Ser Gly Gly Gly Leu Val Gln Pro Gly Gly Ser Leu Arg Leu Ser

Cys Ala Ala Ser Gly Phe Thr Phe Ser Ser Tyr Thr Met Ser Trp Val Arg Gln Ala Pro Gly Lys

Gly Leu Glu Trp Val Ala Thr Ile Ser Gly Gly Gly Phe Gly Thr Tyr Tyr Pro Asp Ser Val Lys

Gly Arg Phe Thr Ile Ser Arg Asp Asn Ala Lys Asn Ser Leu Tyr Leu Gln Met Asn Ser Leu

Arg Ala Glu Asp Thr Ala Val Tyr Tyr Cys Ala Arg Pro Gly Tyr His Asn Tyr Tyr Phe Asp Ile

Trp Gly Gln Gly Thr Thr Val Thr Val Ser Ser Ala Ser Thr Lys Gly Pro Ser Val Phe Pro Leu

Ala Pro Cys Ser Arg Ser Thr Ser Glu Ser Thr Ala Ala Leu Gly Cys Leu Val Lys Asp Tyr Phe

Pro Glu Pro Val Thr Val Ser Trp Asn Ser Gly Ala Leu Thr Ser Gly Val His Thr Phe Pro Ala

Val Leu Gln Ser Ser Gly Leu Tyr Ser Leu Ser Ser Val Val Thr Val Pro Ser Ser Ser Leu Gly

Thr Lys Thr Tyr Thr Cys Asn Val Asp His Lys Pro Ser Asn Thr Lys Val Asp Lys Arg Val

Glu Ser Lys Tyr Gly Pro Pro Cys Pro Pro Cys Pro Ala Pro Glu Ala Ala Gly Gly Pro Ser Val

Phe Leu Phe Pro Pro Lys Pro Lys Asp Thr Leu Met Ile Ser Arg Thr Pro Glu Val Thr Cys Val

Val Val Asp Val Ser Gln Glu Asp Pro Glu Val Gln Phe Asn Trp Tyr Val Asp Gly Val Glu

Val His Asn Ala Lys Thr Lys Pro Arg Glu Glu Gln Phe Asn Ser Thr Tyr Arg Val Val Ser Val

Leu Thr Val Leu His Gln Asp Trp Leu Asn Gly Lys Glu Tyr Lys Cys Lys Val Ser Asn Lys

Gly Leu Pro Ser Ser Ile Glu Lys Thr Ile Ser Lys Ala Lys Gly Gln Pro Arg Glu Pro Gln Val

Tyr Thr Leu Pro Pro Ser Gln Glu Glu Met Thr Lys Asn Gln Val Ser Leu Thr Cys Leu Val

Lys Gly Phe Tyr Pro Ser Asp Ile Ala Val Glu Trp Glu Ser Asn Gly Gln Pro Glu Asn Asn Tyr

Lys Thr Thr Pro Pro Val Leu Asp Ser Asp Gly Ser Phe Phe Leu Tyr Ser Arg Leu Thr Val

Asp Lys Ser Arg Trp Gln Glu Gly Asn Val Phe Ser Cys Ser Val Met His Glu Ala Leu His

Asn His Tyr Thr Gln Lys Ser Leu Ser Leu Ser Leu Gly

LC (SEQ ID NO: 25)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Gly Arg Gln Ser Ile Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Ala Ser Trp Pro Leu His Phe Gly Gly Gly Thr Lys Val Glu Ile Lys Arg Thr Val

Ala Ala Pro Ser Val Phe Ile Phe Pro Pro Ser Asp Glu Gln Leu Lys Ser Gly Thr Ala Ser Val

Val Cys Leu Leu Asn Asn Phe Tyr Pro Arg Glu Ala Lys Val Gln Trp Lys Val Asp Asn Ala

-continued

Leu Gln Ser Gly Asn Ser Gln Glu Ser Val Thr Glu Gln Asp Ser Lys Asp Ser Thr Tyr Ser Leu

Ser Ser Thr Leu Thr Leu Ser Lys Ala Asp Tyr Glu Lys His Lys Val Tyr Ala Cys Glu Val Thr

His Gln Gly Leu Ser Ser Pro Val Thr Lys Ser Phe Asn Arg Gly Glu Cys

LC (SEQ ID NO: 26)

Glu Ile Val Leu Thr Gln Ser Pro Ala Thr Leu Ser Leu Ser Pro Gly Glu Arg Ala Thr Leu Ser

Cys His Ala Ser Asp Ser Ile Ser Asn Ser Leu His Trp Tyr Gln Gln Lys Pro Gly Gln Ala Pro

Arg Leu Leu Ile Tyr Tyr Ala Arg Gln Ser Glu Gln Gly Ile Pro Ala Arg Phe Ser Gly Ser Gly

Ser Gly Thr Asp Phe Thr Leu Thr Ile Ser Ser Leu Glu Pro Glu Asp Phe Ala Val Tyr Tyr Cys

Gln Gln Ser Ala Ser Trp Pro Leu His Phe Gly Gly Gly Thr Lys Val Glu Ile Lys Arg Thr Val

Ala Ala Pro Ser Val Phe Ile Phe Pro Pro Ser Asp Glu Gln Leu Lys Ser Gly Thr Ala Ser Val

Val Cys Leu Leu Asn Asn Phe Tyr Pro Arg Glu Ala Lys Val Gln Trp Lys Val Asp Asn Ala

Leu Gln Ser Gly Asn Ser Gln Glu Ser Val Thr Glu Gln Asp Ser Lys Asp Ser Thr Tyr Ser Leu

Ser Ser Thr Leu Thr Leu Ser Lys Ala Asp Tyr Glu Lys His Lys Val Tyr Ala Cys Glu Val Thr

His Gln Gly Leu Ser Ser Pro Val Thr Lys Ser Phe Asn Arg Gly Glu Cys

Human Dkk-1 Amino Acid Sequence (SEQ ID NO: 27)

Thr Leu Asn Ser Val Leu Asn Ser Asn Ala Ile Lys Asn Leu Pro Pro Pro Leu Gly Gly Ala Ala

Gly His Pro Gly Ser Ala Val Ser Ala Ala Pro Gly Ile Leu Tyr Pro Gly Gly Asn Lys Tyr Gln

Thr Ile Asp Asn Tyr Gln Pro Tyr Pro Cys Ala Glu Asp Glu Glu Cys Gly Thr Asp Glu Tyr

Cys Ala Ser Pro Thr Arg Gly Gly Asp Ala Gly Val Gln Ile Cys Leu Ala Cys Arg Lys Arg

Arg Lys Arg Cys Met Arg His Ala Met Cys Cys Pro Gly Asn Tyr Cys Lys Asn Gly Ile Cys

Val Ser Ser Asp Gln Asn His Phe Arg Gly Glu Ile Glu Glu Thr Ile Thr Glu Ser Phe Gly Asn

Asp His Ser Thr Leu Asp Gly Tyr Ser Arg Arg Thr Thr Leu Ser Ser Lys Met Tyr His Thr Lys

Gly Gln Glu Gly Ser Val Cys Leu Arg Ser Ser Asp Cys Ala Ser Gly Leu Cys Cys Ala Arg

His Phe Trp Ser Lys Ile Cys Lys Pro Val Leu Lys Glu Gly Gln Val Cys Thr Lys His Arg Arg

Lys Gly Ser His Gly Leu Glu Ile Phe Gln Arg Cys Tyr Cys Gly Glu Gly Leu Ser Cys Arg Ile

Gln Lys Asp His His Gln Ala Ser Asn Ser Ser Arg Leu His Thr Cys Gln Arg His

---

The invention claimed is:

1. A method of treating a subject suffering from a cancer, comprising the steps of:

obtaining a sample of a cancer cell from the subject;

determining that the subject has a constitutively activating mutation in a beta-catenin protein (SEQ ID NO: 2) in the sample; and administering to the subject determined to have the constitutively activating mutation in a beta-catenin protein (SEQ ID NO: 2) an effective amount of an anti-Dkk-1 antibody or antigen binding-fragment thereof, wherein the cancer is an esophageal cancer or a uterine cancer, and wherein the anti-Dkk-1 antibody or antigen binding-fragment thereof comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2 and HCDR3, wherein LCDR1 has the amino sequence of SEQ ID NO: 6, LCDR2 has the amino sequence of SEQ ID NO: 7, LCDR3 has the amino sequence of SEQ ID NO: 8, HCDR1 has the amino sequence of SEQ ID NO: 9, HCDR2 has the amino sequence of SEQ ID NO: 10, and an HCDR3 has the amino sequence of SEQ ID NO: 11.

2. The method of claim 1, further including administering an effective amount of a chemotherapeutic agent.

3. The method of claim 2, wherein the chemotherapeutic agent is a taxane, paclitaxel, docetaxel, carbazitaxel, gemcitabine, carboplatin, cisplatin, oxaliplatin, fluorouracil, capecitabine, or tegafur, or any functional analog thereof.

4. The method of claim 1, wherein the LCVR comprises the amino acid sequence of SEQ ID NO: 12 and the HCVR comprises the amino acid sequence of SEQ ID NO: 13.

5. The method of claim 1, wherein the LCVR and HCVR comprise amino acid sequences selected from the group consisting of: (i) a LCVR comprising the amino acid sequence of SEQ ID NO: 14 and a HCVR comprising the amino acid sequence of SEQ ID NO: 15; (ii) a LCVR comprising the amino acid sequence of SEQ ID NO: 16 and a HCVR comprising the amino acid sequence of SEQ ID NO: 17; (iii) a LCVR comprising the amino acid sequence of SEQ ID NO: 18 and a HCVR comprising the amino acid sequence of SEQ ID NO: 15; (iv) a LCVR comprising the amino acid sequence of SEQ ID NO: 19 and a HCVR comprising the amino acid sequence of SEQ ID NO: 15.

6. The method of claim 5, wherein the LCVR comprises the amino acid sequence of SEQ ID NO: 16 and the HCVR comprises the amino acid sequence of SEQ ID NO: 17.

7. The method of claim 6, wherein the anti-Dkk-1 antibody comprises a heavy chain and a light chain amino acid sequence selected from the group consisting of a) a heavy chain comprising the amino acid sequence of SEQ ID NO: 24 and light chain comprising the amino acid sequence of SEQ ID NO: 21, b) a heavy chain comprising the amino acid sequence of SEQ ID NO: 22 and a light chain comprising the amino acid sequence of SEQ ID NO: 23, c) a heavy chain comprising the amino acid sequence of SEQ ID NO: 24 and a light chain comprising the amino acid sequence of SEQ ID NO: 25, and d) a heavy chain comprising the amino acid sequence of SEQ ID NO: 24 and a light chain comprising the amino acid sequence of SEQ ID NO: 26.

8. The method of claim 7, wherein the anti-Dkk-1 antibody comprises a heavy chain comprising the amino acid sequence of SEQ ID NO: 22 and a light chain comprising the amino acid sequence of SEQ ID NO: 23.

9. The method of claim 1, wherein the mutation includes a deletion of exon 3 (SEQ ID NO: 4).

10. The method of claim 9, wherein the mutation includes a deletion of Exons 2, 3, and 4 (SEQ ID NOs. 3, 4, and 5).

11. The method of claim 1 wherein the mutation includes a deletion within exon 3 (SEQ ID NO: 4).

12. The method of claim 1, wherein the mutation is a deletion of any subsequence within the amino acid sequence of the protein of SEQ ID NO: 2, wherein said subsequence includes at least one residue selected from Ser33, Ser37, Thr41, and Ser45.

13. The method of claim 1, wherein the mutation is a mutation of any one of the amino acid residues selected from Ser33, Ser37, Thr41, and Ser45 of the protein of SEQ ID NO: 2.

* * * * *

UNITED STATES PATENT AND TRADEMARK OFFICE

CERTIFICATE OF CORRECTION

PATENT NO. : 11,267,876 B2
APPLICATION NO. : 16/345191
DATED : March 8, 2022
INVENTOR(S) : Michael H. Kagey et al.

It is certified that error appears in the above-identified patent and that said Letters Patent is hereby corrected as shown below:

In the Claims

At Column 69, Claim number 1, Line numbers 55-61:
"HCDR2 and HCDR3, wherein LCDRI has the amino sequence of SEQ ID NO: 6, LCDR2 has the amino sequence of SEQ ID NO: 7, LCDR3 has the amino sequence of SEQ ID NO: 8, HCDRI has the amino sequence of SEQ ID NO: 9, HCDR2 has the amino sequence of SEQ ID NO: 10, and an HCDR3 has the amino sequence of SEQ ID NO: 11."

Should read:
-- HCDR2 and HCDR3, wherein LCDRI has the amino acid sequence of SEQ ID NO: 6, LCDR2 has the amino acid sequence of SEQ ID NO: 7, LCDR3 has the amino acid sequence of SEQ ID NO: 8, HCDRI has the amino acid sequence of SEQ ID NO: 9, HCDR2 has the amino acid sequence of SEQ ID NO: 10, and an HCDR3 has the amino acid sequence of SEQ ID NO: 11. --

Signed and Sealed this
Seventeenth Day of September, 2024

Katherine Kelly Vidal

Katherine Kelly Vidal
*Director of the United States Patent and Trademark Office*